US012544550B2

(12) United States Patent
Jiang et al.

(10) Patent No.: US 12,544,550 B2
(45) Date of Patent: Feb. 10, 2026

(54) DISINFECTING CAP WITH PRESSURE SEAL CAPABILITY

(71) Applicant: Becton, Dickinson and Company, Franklin Lakes, NJ (US)

(72) Inventors: Chang Jiang, Butler, NJ (US); Kevin M. Ryan, Whitehouse Station, NJ (US); Michael Kwong Chan, New York, NY (US); Daniel Benjamin DiMirco, Scarsdale, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1009 days.

(21) Appl. No.: 17/631,581

(22) PCT Filed: Aug. 5, 2020

(86) PCT No.: PCT/US2020/044942

§ 371 (c)(1),
(2) Date: Jan. 31, 2022

(87) PCT Pub. No.: WO2021/030105

PCT Pub. Date: Feb. 18, 2021

(65) Prior Publication Data

US 2022/0331575 A1 Oct. 20, 2022

Related U.S. Application Data

(60) Provisional application No. 62/884,783, filed on Aug. 9, 2019.

(51) Int. Cl.
*A61M 39/20* (2006.01)
*A61M 39/16* (2006.01)
*A61M 39/10* (2006.01)

(52) U.S. Cl.
CPC .......... *A61M 39/20* (2013.01); *A61M 39/162* (2013.01); *A61M 2039/1038* (2013.01)

(58) Field of Classification Search
CPC ............................ A61M 39/20; A61M 39/162
See application file for complete search history.

(56) References Cited

U.S. PATENT DOCUMENTS 4,597,758 A 7/1986 Aalto et al.
4,711,363 A 12/1987 Marino
(Continued)

FOREIGN PATENT DOCUMENTS

CA 2523133 C 2/2013
CN 1322119 A 11/2001
(Continued)

OTHER PUBLICATIONS

"Ruhof Dry Sponges", Ruhof, Sep. 30, 2016, https://www.ruhof.com/products/ruhof-dry-sponges (Year: 2016).
(Continued)

*Primary Examiner* — Donald R Spamer
(74) *Attorney, Agent, or Firm* — Servilla Whitney LLC

(57) ABSTRACT

A cap is described for connection to a needleless connector having an open lumen, the cap includes a housing having a top wall and sidewall forming a first cavity, an insert, an absorbent reservoir material and a sealing foam. The insert includes an inner thread on an inner surface, the inner thread being sufficient to interlock with a mating feature of a female needleless connector. The inner surface of the insert defines a second cavity. The protrusion/insert includes an outer thread on an outer surface, the outer thread being sufficient to interlock with a mating feature of a male needleless connector. The second cavity configured to define a chamber to contain an absorbent reservoir material, a sealing foam and disinfectant or antimicrobial agent.

20 Claims, 21 Drawing Sheets

(56) References Cited

U.S. PATENT DOCUMENTS

| | | | |
|---|---|---|---|
| 4,738,376 | A | 4/1988 | Markus |
| 5,496,288 | A | 3/1996 | Sweeney |
| 5,676,406 | A | 10/1997 | Simmons et al. |
| 6,632,199 | B1 | 10/2003 | Tucker et al. |
| 8,388,894 | B2 | 3/2013 | Colantonio |
| 8,715,231 | B2 | 5/2014 | Woehr |
| 8,721,627 | B2 | 5/2014 | Alpert et al. |
| 9,039,989 | B2 | 5/2015 | Liu et al. |
| 9,132,223 | B1 | 9/2015 | Wakeel |
| 9,192,449 | B2 | 11/2015 | Kerr et al. |
| 10,099,048 | B2 | 10/2018 | Chiu et al. |
| 10,166,381 | B2 | 1/2019 | Gardner et al. |
| 10,376,686 | B2 | 8/2019 | Burkholz et al. |
| 10,871,246 | B2 | 12/2020 | Marici et al. |
| 11,353,147 | B2 | 6/2022 | Marici |
| 11,511,100 | B2 | 11/2022 | Ryan |
| 11,628,288 | B1 | 4/2023 | Solomon et al. |
| 2003/0144647 | A1 | 7/2003 | Miyahara |
| 2004/0039341 | A1 | 2/2004 | Ranalletta |
| 2004/0044318 | A1 | 3/2004 | Fiser et al. |
| 2005/0147525 | A1 | 7/2005 | Bousquet |
| 2005/0197646 | A1 | 9/2005 | Connell et al. |
| 2007/0060904 | A1 | 3/2007 | Vedrine et al. |
| 2007/0129705 | A1 | 6/2007 | Trombley, III et al. |
| 2008/0010766 | A1 | 1/2008 | Kaufman et al. |
| 2008/0177250 | A1 | 7/2008 | Howlett et al. |
| 2009/0205151 | A1 | 8/2009 | Fisher et al. |
| 2010/0003067 | A1 | 1/2010 | Shaw et al. |
| 2010/0020017 | A1 | 1/2010 | Chung |
| 2010/0049170 | A1 | 2/2010 | Solomon et al. |
| 2010/0050351 | A1 | 3/2010 | Colantonio et al. |
| 2010/0100056 | A1 | 4/2010 | Cawthon et al. |
| 2011/0046603 | A1 | 2/2011 | Felsovalyi et al. |
| 2011/0054440 | A1 | 3/2011 | Lewis |
| 2011/0213341 | A1 | 9/2011 | Solomon et al. |
| 2011/0264037 | A1 | 10/2011 | Foshee et al. |
| 2012/0039764 | A1 | 2/2012 | Solomon et al. |
| 2012/0111368 | A1 | 5/2012 | Rahimy et al. |
| 2012/0123386 | A1 | 5/2012 | Tsals |
| 2012/0210678 | A1* | 8/2012 | Alcouloumre ..... A61B 17/3217 206/370 |
| 2012/0302997 | A1 | 11/2012 | Gardner et al. |
| 2013/0085474 | A1 | 4/2013 | Charles et al. |
| 2013/0171030 | A1 | 7/2013 | Ferlic et al. |
| 2013/0197485 | A1 | 8/2013 | Gardner et al. |
| 2013/0338644 | A1 | 12/2013 | Solomon et al. |
| 2014/0052074 | A1 | 2/2014 | Tekeste |
| 2014/0150832 | A1 | 6/2014 | Rogers et al. |
| 2014/0366914 | A1 | 12/2014 | Kerr et al. |
| 2015/0011936 | A1 | 1/2015 | Okihara et al. |
| 2015/0094666 | A1 | 4/2015 | Bates et al. |
| 2016/0045629 | A1 | 2/2016 | Gardner et al. |
| 2016/0067422 | A1 | 3/2016 | Davis et al. |
| 2016/0158520 | A1 | 6/2016 | Ma et al. |
| 2017/0203092 | A1 | 7/2017 | Ryan et al. |
| 2018/0085568 | A1 | 3/2018 | Drmanovic |
| 2018/0200145 | A1 | 7/2018 | Sanders et al. |
| 2018/0200500 | A1 | 7/2018 | Ziebol et al. |
| 2018/0214684 | A1 | 8/2018 | Avula et al. |
| 2018/0237190 | A1 | 8/2018 | Iwasaki |
| 2018/0243547 | A1 | 8/2018 | Fox et al. |
| 2018/0256881 | A1 | 9/2018 | Hitchcock et al. |
| 2018/0256883 | A1 | 9/2018 | Follman et al. |
| 2019/0001115 | A1 | 1/2019 | Ma et al. |
| 2019/0099593 | A1 | 4/2019 | Avula et al. |
| 2019/0151643 | A1 | 5/2019 | Alpert |
| 2019/0234540 | A1* | 8/2019 | Marici .................. A61M 39/20 |
| 2019/0308006 | A1 | 10/2019 | Erekovcanski et al. |
| 2019/0351212 | A1 | 11/2019 | Dudar et al. |
| 2020/0147360 | A1 | 5/2020 | Arnett et al. |
| 2021/0100996 | A1 | 4/2021 | Wijesuriya et al. |
| 2021/0187267 | A1 | 6/2021 | Jiang |
| 2022/0273931 | A1 | 9/2022 | Jiang et al. |
| 2023/0080687 | A1 | 3/2023 | Ryan |

FOREIGN PATENT DOCUMENTS

| | | | |
|---|---|---|---|
| CN | 101535701 | A | 9/2009 |
| CN | 101980746 | A | 2/2011 |
| CN | 201807018 | U | 4/2011 |
| CN | 102172424 | A | 9/2011 |
| CN | 102188766 | A | 9/2011 |
| CN | 102448502 | A | 5/2012 |
| CN | 103083767 | A | 5/2013 |
| CN | 204161736 | U | 2/2015 |
| CN | 206198472 | U | 5/2017 |
| CN | 215653405 | U | 1/2022 |
| CN | 216022674 | U | 3/2022 |
| CN | 216258735 | U | 4/2022 |
| CN | 110090354 | B | 1/2023 |
| DE | 20017013 | U1 | 12/2000 |
| DE | 10247963 | A1 | 5/2004 |
| EP | 0589379 | A1 | 3/1994 |
| EP | 2606930 | A1 | 6/2013 |
| EP | 2832391 | A1 | 2/2015 |
| EP | 3275490 | A1 | 1/2018 |
| GB | 2408259 | A | 5/2005 |
| GB | 2518646 | A | 4/2015 |
| JP | S5841561 | A | 3/1983 |
| JP | H03139363 | A | 6/1991 |
| JP | H04501672 | A | 3/1992 |
| JP | 2001502191 | A | 2/2001 |
| JP | 2001521792 | A | 11/2001 |
| JP | 2004208740 | A | 7/2004 |
| JP | 2008239164 | A | 10/2008 |
| JP | 2008253775 | A | 10/2008 |
| JP | 2009526241 | A | 7/2009 |
| JP | 2010527276 | A | 8/2010 |
| JP | 2012522593 | A | 9/2012 |
| JP | 2013509274 | A | 3/2013 |
| JP | 2013252165 | A | 12/2013 |
| JP | 2014528288 | A | 10/2014 |
| JP | 2014532517 | A | 12/2014 |
| JP | 2015517377 | A | 6/2015 |
| JP | 2016511111 | A | 4/2016 |
| JP | 2016511119 | A | 4/2016 |
| JP | 2016104214 | A | 6/2016 |
| JP | 2019531814 | A | 11/2019 |
| JP | 7419237 | B2 | 1/2024 |
| WO | 200024442 | A1 | 5/2000 |
| WO | 200224551 | A1 | 3/2002 |
| WO | 2011066586 | A1 | 6/2011 |
| WO | 2012144026 | A1 | 10/2012 |
| WO | 2013046857 | A1 | 4/2013 |
| WO | 2014159346 | A1 | 10/2014 |
| WO | 2015004728 | A1 | 1/2015 |
| WO | 2015127285 | A1 | 8/2015 |
| WO | 2015174953 | A1 | 11/2015 |
| WO | 2016158144 | A1 | 10/2016 |
| WO | 2017087400 | A1 | 5/2017 |
| WO | 2018106508 | A1 | 6/2018 |
| WO | 2018237090 | A1 | 12/2018 |
| WO | 2019147906 | A1 | 8/2019 |
| WO | 2019152482 | A1 | 8/2019 |
| WO | 2020056120 | A1 | 3/2020 |
| WO | 2020112767 | A1 | 6/2020 |

OTHER PUBLICATIONS

Final Office Action in U.S. Appl. No. 17/229,173 dated May 22, 2024, 28 pages.

Non-Final Office Action in U.S. Appl. No. 16/923,238 dated Feb. 28, 2024, 18 pages.

Non-Final Office Action in U.S. Appl. No. 17/992,169 dated May 8, 2024, 13 pages.

PCT International Search Report and Written Opinion in PCT/US2020/044942 dated Oct. 16, 2020, 15 pages.

Curos Jet Disinfecting Caps Owner: Curos Disinfecting Port Protectors Link: https://youtu.be/PWlent6_UHs?si=kUVKopzFlpki78H7.

* cited by examiner

DISINFECTING CAP WITH PRESSURE SEAL CAPABILITY

CROSS-REFERENCE TO RELATED APPLICATIONS

This application is the National Stage entry of PCT/US2020/044942, filed on Aug. 5, 2020, which claims priority to U.S. Provisional Application Ser. No. 62/884,783, filed Aug. 9, 2019, the entire disclosures of which are hereby incorporated by reference herein.

TECHNICAL FIELD

The present disclosure generally relates to a device for disinfecting and sterilizing access ports with open lumens, e.g., intravenous male connectors and stopcocks. Generally, exemplary embodiments of the present disclosure relate to the fields of medical caps and medical disinfection caps, and in particular caps and/or disinfection caps for uses with fluid luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub, connection, port or valve is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance and the level of disinfection attributed to this practice typically relies on the ability and competency of the user. In addition to a lack of compliance to "scrubbing the hub", it has also been noted through clinician interviews that there is often a variation in scrub time, dry time and the number of times the needleless connector is scrubbed.

In the example of medical applications, various conventional caps for closing off a needleless connector while not in use have been known for some time in order to decrease Catheter-related bloodstream infection (CRBSI). Even though currently available needleless connectors have septa to close fluid path, caps for disinfecting stopcocks and IV male connectors which have open lumens need mechanisms to hold fluid pressure in the lines to prevent fluid leakage. Additionally, disinfectants typically have a threshold limit for systemic exposure for infusion into blood stream due to biotoxicity of the disinfectants at high dosage. Thus, there is a need for a disinfecting device capable of blocking lumen of open luers to facilitate the mitigation of such disinfectant ingress into connectors, thereby reducing risk of the disinfectant entering the blood stream.

SUMMARY

One aspect of the present disclosure pertains to a cap having a housing including a top wall, an essentially cylindrical sidewall forming a first cavity, and an open bottom formed by the cylindrical sidewall with an opening to the first cavity within the housing for receiving a needleless connector having an open lumen. The cap also includes an insert disposed in the housing and positioned within the first cavity. The insert has an inner surface and an outer surface, the inner surface of the insert defining a second cavity. The insert has an inner thread on the inner surface of the insert and an outer thread on the outer surface of the insert. The cap also includes an absorbent reservoir material disposed under radial compression by the inner thread on the inner surface of the insert. The cap also includes a sealing foam disposed onto the absorbent reservoir material.

In one or more embodiments, the absorbent reservoir material is a nonwoven material, foam, or a sponge. In one or more embodiments, the absorbent reservoir material is soaked with a disinfectant or an antimicrobial agent.

In one or more embodiments, the sealing foam is made of a closed cell foam, a polyethylene foam, a thermoplastic elastomer, a rubber or rubber like foams. In one or more specific embodiments, the sealing foam is an EPDM sponges, EVA, Buna-N, silicone, vinyl, neoprene, fluoroelastomers, gum rubber.

In one or more embodiments, the insert extends essentially from an inner surface of the top wall toward the open bottom of the housing. In one or more embodiments, the insert extends essentially parallel to the sidewall of the housing. In one or more embodiments, the inner thread and the outer thread have an inclined thread pattern. In one or more embodiments, the inner thread and outer thread have a helical-shaped thread pattern.

In one or more embodiments, the exterior wall surface of the sidewall of the housing includes a plurality of grip members.

In one or more embodiments, the cap further includes a disinfectant or the antimicrobial agent.

In one or more embodiments, the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the housing is made of a high density polyethylene or polypropylene material. In one or more embodiments, the housing has an average wall thickness of >0.03 inches.

In one or more embodiments, the cap includes a peelable seal. In one or more embodiments, the peelable seal comprises an aluminum or multi-layer polymer film. In one or more embodiments, the peelable seal further comprises a moisture barrier.

A second aspect of the present disclosure pertains to a cap having a housing comprising a top wall, an essentially cylindrical sidewall forming a first cavity, and an open bottom formed by the cylindrical sidewall with an opening to the first cavity within the housing for receiving a needleless connector having an open lumen; and an insert disposed within the first cavity, the insert having closed distal end comprising a distal wall, an open proximal end, a sidewall extending proximally from the distal wall toward the open proximal end, the sidewall having a split-thread insert integrally formed with the distal wall, the split-thread protrusion/insert having an inner surface and an outer surface, the inner surface of the split-thread protrusion/insert defining a second cavity, an inner thread on the inner surface of the split-thread protrusion/insert, the inner thread being sufficient to interlock with a mating feature of the female needleless connector, an outer thread on the outer surface of the split-thread protrusion/insert, the outer thread being sufficient to interlock with a mating feature of the male needleless connector; a piston-shaped sealing foam; absorbent material configured within the second cavity; a disinfectant or an antimicrobial agent; and forming a seal for maintaining the disinfectant or an antimicrobial agent within the second cavity prior to use of the cap.

In one or more embodiments, the sealing foam is made of a closed cell foam, a polyethylene foam, a thermoplastic elastomer, a rubber or rubber like foams. In one or more specific embodiments, the sealing foam is an EPDM sponges, EVA, Buna-N, silicone, vinyl, neoprene, fluoroelastomers, gum rubber.

In one or more embodiments, the absorbent reservoir material includes a centrally disposed through hole extending from a distal end to a proximal end of the absorbent reservoir material.

In one or more embodiments, the elongate shaft of the sealing foam is disposed into the though hole of the absorbent reservoir material.

In one or more embodiments, the absorbent reservoir material surrounds an elongate shaft of the sealing foam.

In one or more embodiments, the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

In one or more embodiments, the housing is made of a high density polyethylene or polypropylene material. In one or more embodiments, the housing has an average wall thickness of >0.03 inches.

In one or more embodiments, the cap includes a peelable seal. The peelable seal may include an aluminum or multi-layer polymer film. In one or more embodiments, the peelable seal may also include a moisture barrier.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Figure 1:
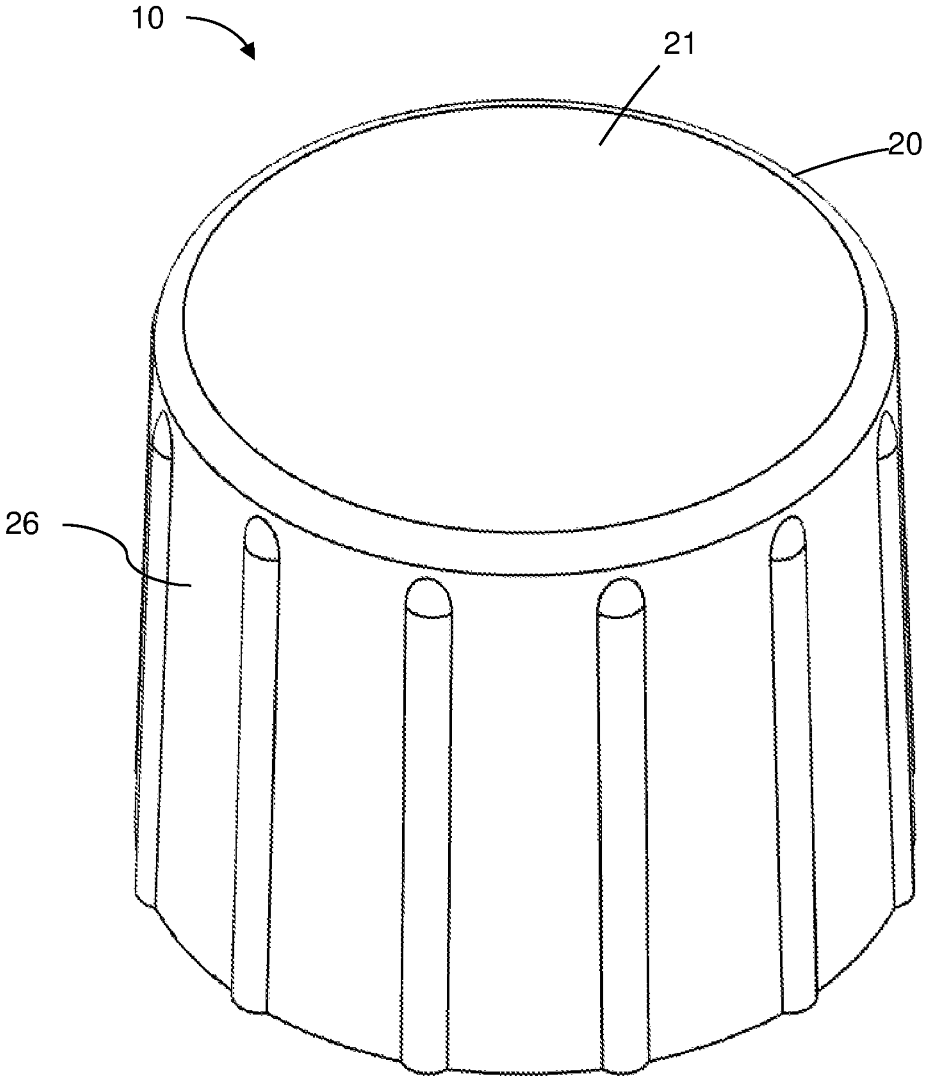
FIG. 1 illustrates a perspective top view of a housing according to a first exemplary embodiments of the disclosure.

Embodiments of the disclosure pertain to a sterile, cap for connection to and disinfection of a medical connector having an open lumen, including male connectors, female connectors and stopcocks. The male connectors and female connectors can be male luer connectors and female luer connectors. Embodiments of the cap comprise a housing, an insert, an absorbent material and a sealing foam. The housing comprises an integral body having a closed end and an open end. The sidewall of the housing having a length $L_C$ extending from the closed end to an open end and defining a chamber. In one or more embodiments, the open end includes an engagement surface. The insert includes an interior wall surface having one or more threads adapted to engage a female luer connector. The exterior wall surface of the insert having one or more threads that are sized and adapted to receive a male luer connector. The cap may further comprise a disinfectant or the antimicrobial agent and a peelable seal. The cap provides a mechanical barrier for connectors and contains an antimicrobial agent for disinfection. The cap of the present disclosure also allows the practitioner to streamline the disinfecting process while blocking the lumen of open luers to facilitate the mitigation of the ingress of contaminants and disinfectant into the open lumens of the connectors, thereby reducing risk of the contaminants and disinfectant entering the blood stream.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "hole", "tip", "hub", "thread", "sponge", "prong", "protrusion/insert", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a cap, connector cap or disinfecting cap includes integrated thread, or threads, and other features in any and all combinations allowing it to interface with both male and female threaded fittings.

According to further exemplary implementations of the embodiments of the present disclosure, configuration of structural elements making up the insert include one or more cantilevered prongs disposed in cap's inner cavity, the cantilevered prongs comprising an inner thread to connect to female medical connectors and an outer thread to connect to male medical connectors, to facilitate securing of the cap onto a female fitting or onto a male fitting, respectively.

According to yet further exemplary implementations of the embodiments of the present disclosure, both of the male and female threads coincide with each other on the inner and outer face of the threaded protrusion/insert.

According to still further exemplary implementations of the embodiments of the present disclosure, the cantilevered prong of the insert may be of a split thread type in which the cantilevered prong of the insert may bend in order to allow better interference fit compliance with the fittings.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Figure 2:
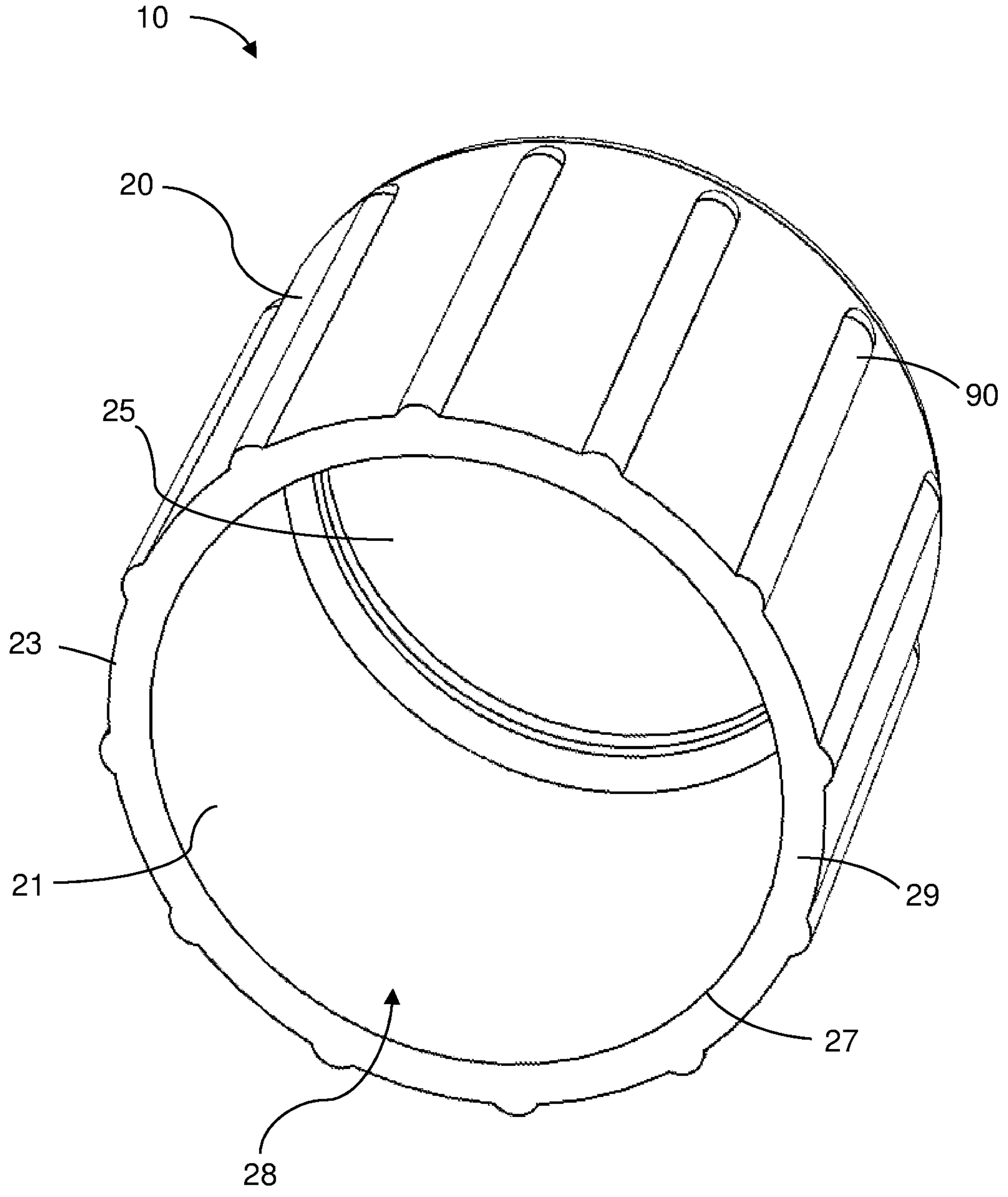
FIG. 2 illustrates a bottom view of the housing as shown in FIG. 1.
Figure 3:
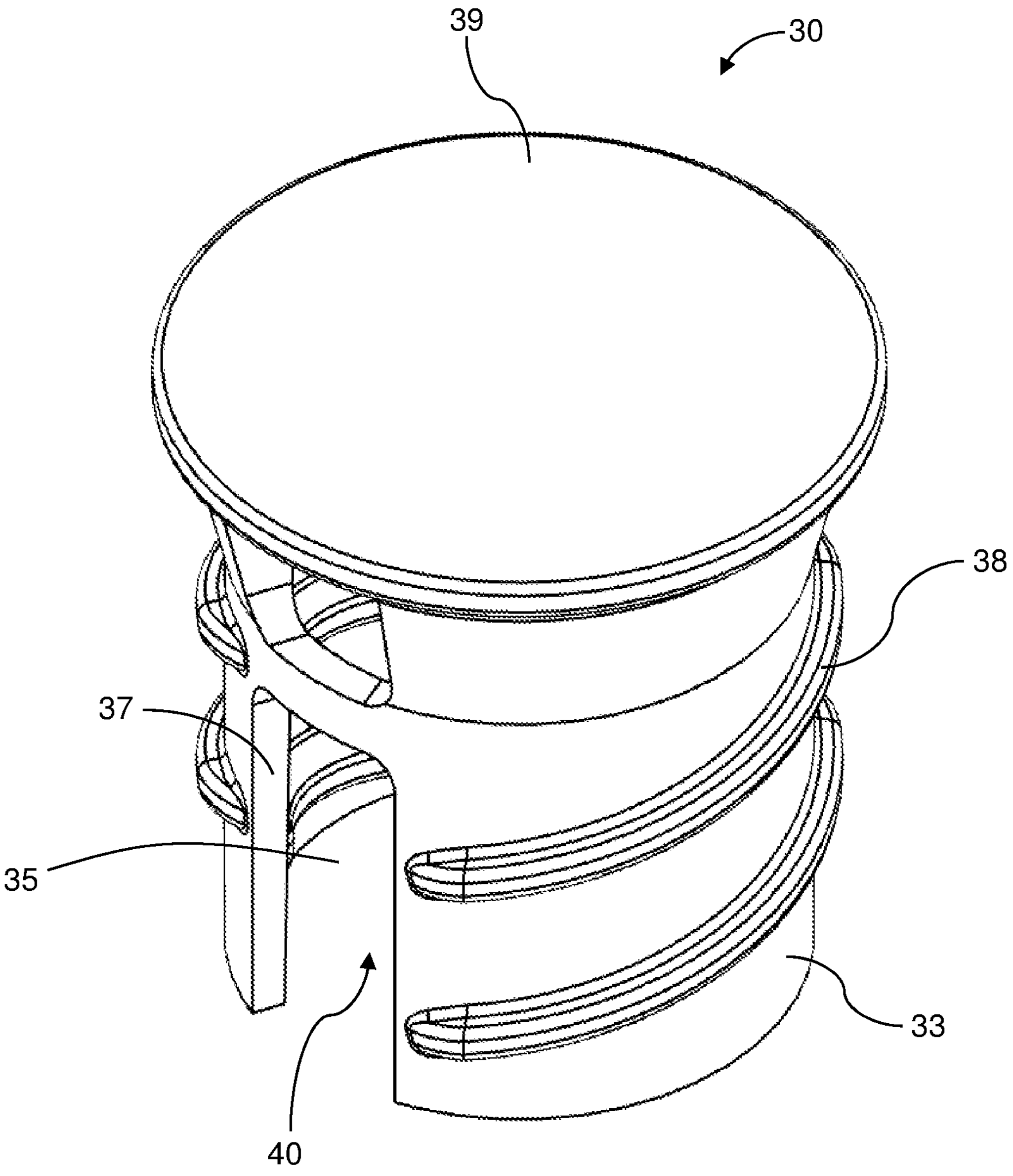
FIG. 3 illustrates a perspective top view of an exemplary insert according to a first embodiment of the disclosure.
Figure 4:
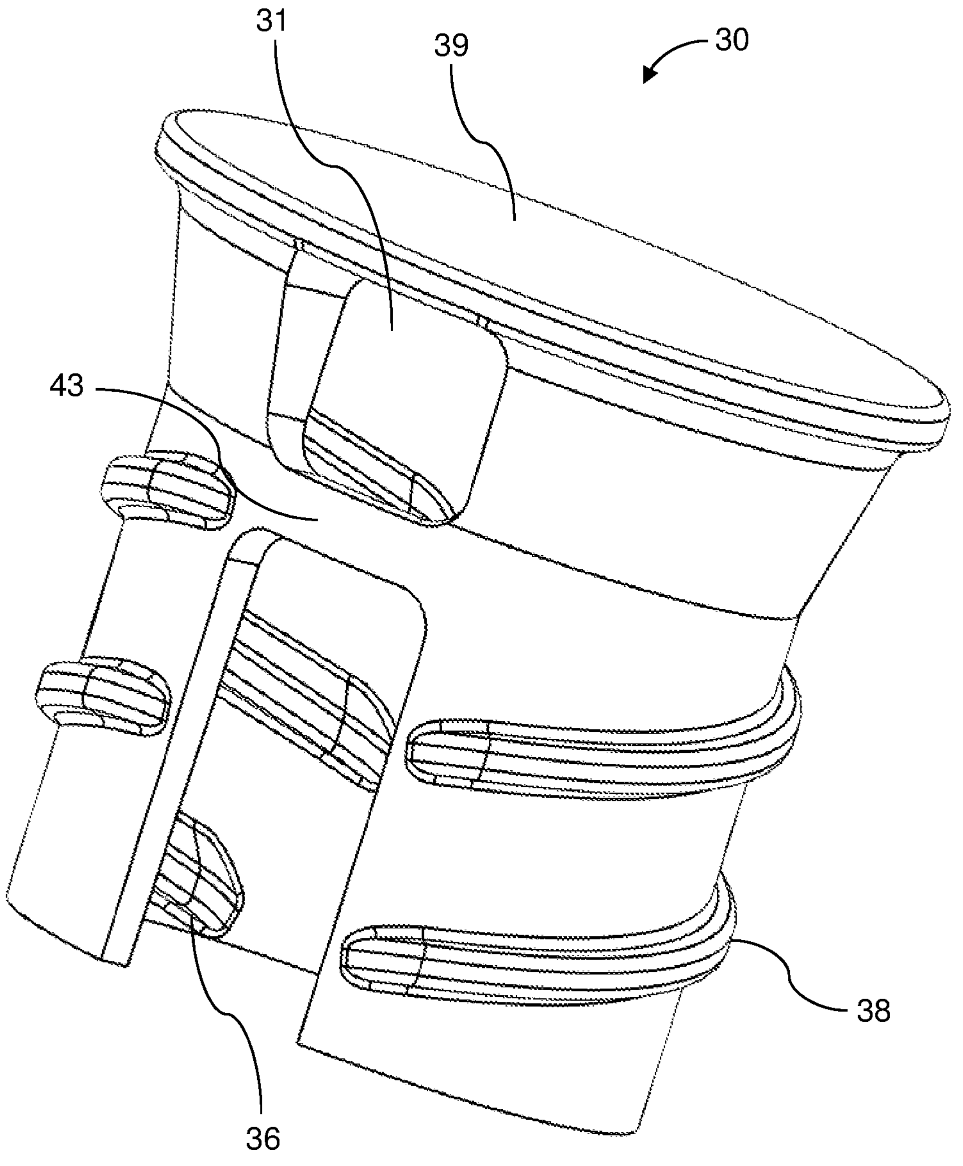
FIG. 4 illustrates a perspective side view of the exemplary insert shown in FIG. 3.
Figure 5:
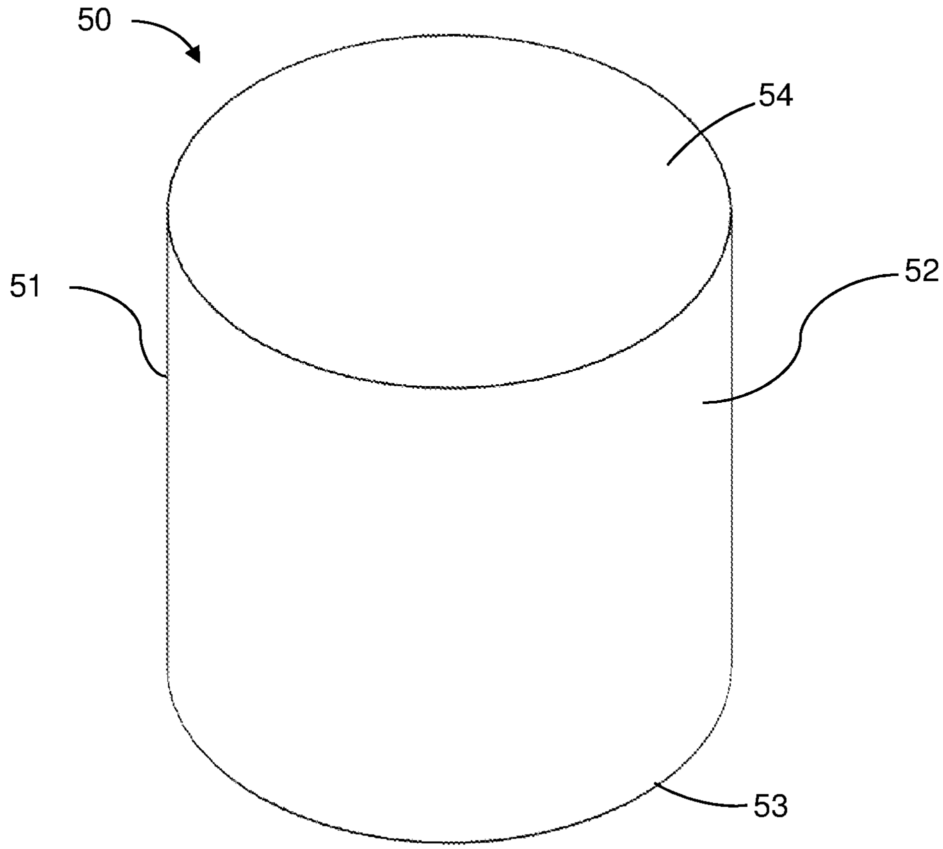
FIG. 5 illustrates a perspective view of an exemplary absorbent reservoir material according to a first exemplary embodiment of the disclosure.
Figure 6:
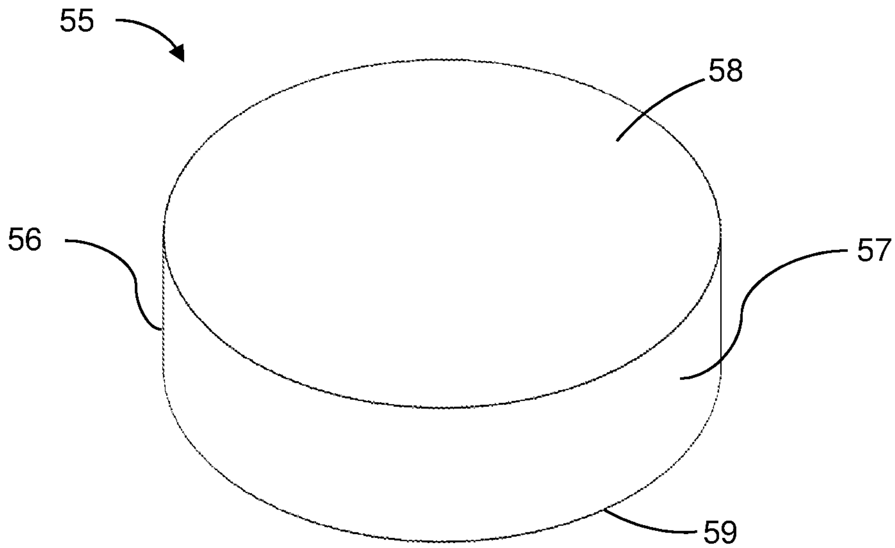
FIG. 6 illustrates a perspective view of an exemplary sealing foam according to a first exemplary embodiment of the disclosure.

A first aspect of the present disclosure relates to a cap 10 including a housing 20 and an insert 30 in the form of a prong or protrusion. As shown in FIGS. 1 and 2, housing 20 can include a top wall 25, an essentially cylindrical sidewall 26 forming a first cavity 28, and an open bottom 23 formed by the cylindrical sidewall 26 with an opening 27 to the first cavity 28 within the housing 20 for receiving a hub of a female needleless connector or a male needleless connector. In one embodiment, the insert 30 is integrally formed with the housing 20, the insert 30 being positioned within the first cavity 28. In another embodiment as shown in FIGS. 3 and 4, the insert 30 includes an inner surface 31 and an outer surface 33, the inner surface 31 of insert 30 defining a second cavity 40.

In one or more embodiments, the insert 30 of the present disclosure has an inner thread 36 that has a size and pitch configured to engage a threadable segment of a female connector, such as for example, a female luer connector. Such connectors are generally and commonly used as catheter and other fluid-tight protective connectors in medical applications. In some embodiments, cap 10 provides a protective cover for a female luer connector when engaged with the connector. Specifically, the cap 10 provides a protective cover when threads from the female luer connector engage and form a releasable connection with the inner threads 36 of insert 30. In one or more embodiments, the inner thread 36 is included on the inner surface 31 of insert 30, the inner thread 36 being sufficient to interlock with a mating feature of the female needleless connector.

In one or more embodiments, an outer thread 38 is included on the outer surface 33 of insert 30, the outer thread 38 being sufficient to interlock with a mating feature of the male needleless connector. In one or more embodiments, as shown in FIG. 3, the insert 30 can include one or more cantilevered prongs 37 separated by one or more respective gaps or cutouts 35. In one or more embodiments, at least one of the cantilevered prongs 37 can be configured to bend to facilitate interference fit between the insert 30 and the mating feature of the male needleless connector or female needleless connector. In one or more embodiments, insert 30 can extend essentially from the top wall 25 toward the open bottom 23 of the housing 20. In one or more embodiments, the insert 30 can extend essentially parallel to the cylindrical sidewall 26 of the housing 20.

Referring to FIGS. 1 and 2, according to exemplary embodiments of the present disclosure a cap 10 comprises a housing 20 which includes a top wall 25 with an inner surface 21, a sidewall 26 (which can be essentially cylindrical) with an inner surface 21, and an opening 27 forming a first cavity 28. An opening 27 is disposed at the open bottom 23 of housing 20.

Figure 7:
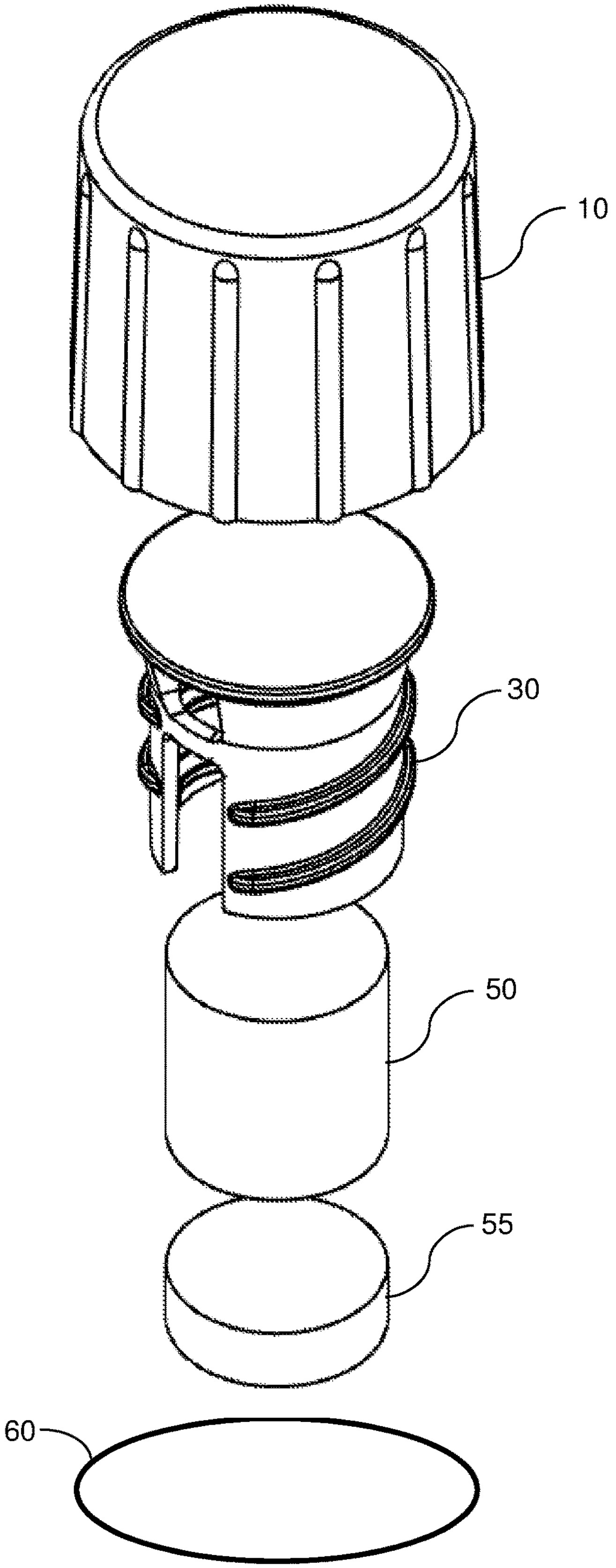
FIG. 7 illustrates an exploded perspective view of an exemplary cap according to one or more embodiments of the disclosure.
Figure 8:
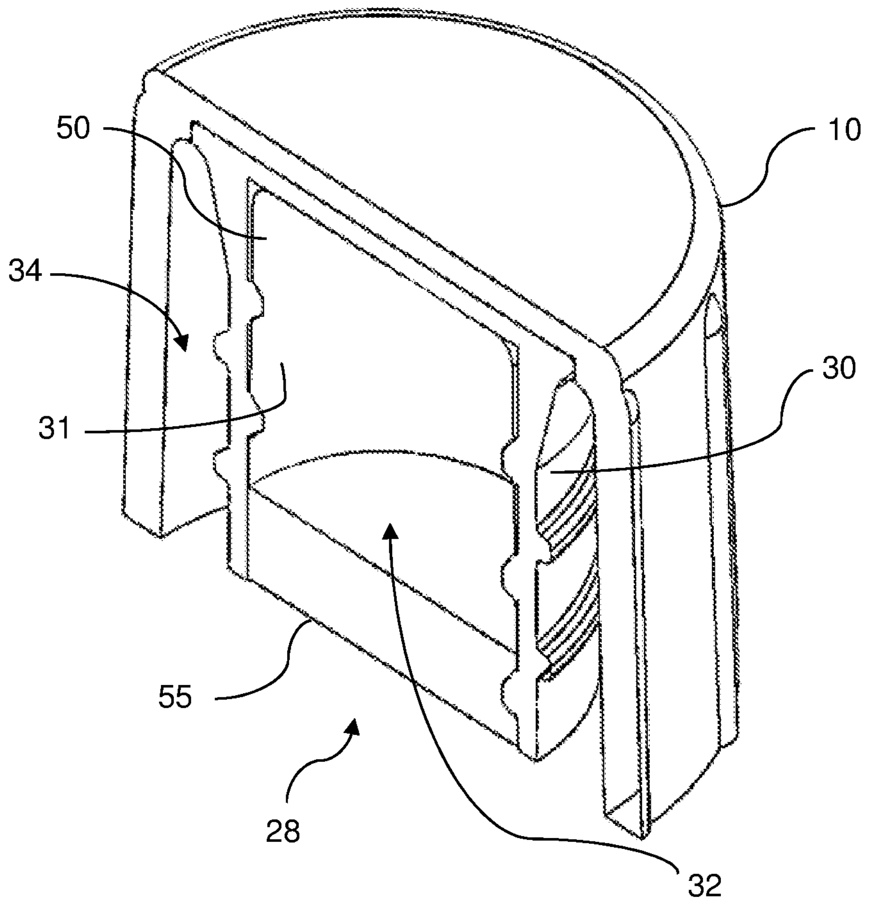
FIG. 8 illustrates a cross-sectional view of an exemplary assembled cap as shown in FIG. 7.

Referring to FIGS. 7 and 8, the insert 30 is disposed within cavity 28 of the housing 20, which can be essentially cylindrical and coaxial with sidewall 26. The insert 30 is disposed within the cavity 28 of the housing includes an inner surface 31 defining an inner portion 32 of cavity 28, and an outer surface 33 defining and outer portion 34 of cavity 28. In one or more embodiments, the closed end 39 of the insert 30 is abutted against the top wall 25 of the housing 20 when disposed in the cavity 28. Insert 30 comprises an inner thread 36 disposed on the inner surface 31 for engaging a male connector and an outer thread 38 on its outer surface 33 for engaging a female connector.

Referring to FIGS. 5 through 8, in one or more embodiments, an absorbent reservoir material 50 disposed within the second cavity 40 is under radial compression by the inner thread 36 on the inner surface 31 of insert 30 to retain the absorbent reservoir material 50 within the inner portion 32. In one or more embodiments, the absorbent reservoir material 50 is a nonwoven material, foam, or a sponge. In a specific embodiment, the foam is a polyurethane foam. In a specific embodiment, the absorbent reservoir material 50 is in the form of a foam plug.

The absorbent reservoir material 50 comprises an integral body 51, an annular wall 52, a bottom surface 53 and a distal face 54. In one or more embodiments, the foam of the absorbent reservoir material 50 is saturated or soaked with a disinfectant or an antimicrobial agent. In one or more embodiments, the absorbent reservoir material 50 is a nonwoven material, foam, or a sponge. In a specific embodiment, the absorbent reservoir material 50 is polyethylene foam. The foam may be open celled, semi-opened or closed celled. In one or more embodiments, the absorbent reservoir material 50 is molded, extruded or die cut from sheeting to form a cylindrical block shape.

In one or more embodiments, as shown in FIGS. 5 through 8, sealing foam 55 is disposed onto absorbent reservoir material 50.

The sealing foam 55 comprises of an integral body 56, an annular wall 57, a bonded surface 58 and a sealing surface 59. In a specific embodiment, the sealing foam 55 is closed cell foam. In one or more embodiments, the sealing foam 55 may comprise of closed cell foams such as PE foams or TPE foams. In one or more embodiment, the sealing foam 55 may also comprise of rubber or rubber-like foams including: EPDM sponges, EVA, Buna-N, polyethylene sponges, silicone, vinyl, neoprene, fluoroelastomers, gum rubber, or TPE materials. In one or more embodiments, the sealing foam 55 is molded, extruded or die cut from sheeting to form a cylindrical block shape.

The bonded surface 58 of the sealing foam 55 is secured to the bottom surface 53 of the absorbent reservoir material 50. When secured, the annular walls (52, 57) of both the sealing foam 55 and the absorbent reservoir material 50 are concentric and coincident. The methods of which the bonded surface 58 and the bottom surface 53 of the absorbent reservoir material 50 are secured include using adhesives, heat welding, ultrasonic welding, and other appropriate bonding methods. The coincident annular wall 52 of the sealing foam 55 and the annular wall 57 of the absorbent reservoir material 50 is appropriately sized to fit into the second cavity 40 of the insert 30 defined by inner surface 31. When assembled, the sealing foam and the reservoir foam completely fill the inner surface 31 of insert 30 defining a second cavity 40. The assembly of the absorbent reservoir material 50 and the sealing foam 55 are frictionally fitted into the second cavity 40 formed by the inner surface 31 of insert 30.

As the threaded fitting of the insert 30 is threadably secured to a luer connector (not shown), the luer connector compresses the sealing surface 59 of the sealing foam 55 towards the closed end 39 of the insert 30. Compression of the sealing foam 55 causes the bonded surface 58 of the sealing foam 55 to compress the absorbent reservoir material 50 further into the closed end 39 of the insert 30. As a needless connector is threadably secured to the inner threads 36 or outer threads 38, the sealing foam 55 applies pressure to the lumen of a luer connector. The pressure applied to the lumen of the connector by the sealing foam 55 blocks the lumen and mitigates the potential of disinfectant ingress into the luer connectors. In one or more embodiments, the sealing foam 55 is elastic. The pressure applied by the sealing foam 55 to the connector can range from less than one psi and up to tens of psi. Additionally, the pressure applied by the sealing foam 55 to the lumen of the luer connector sustains the fluid pressure in the lines of the luer connector to prevent fluid leakage.

In yet another exemplary implementation, a disinfecting member or members, such as an absorbent reservoir material 50, in the form of an isopropyl alcohol (IPA) soaked sponge and/or sponge.

The cap 10 can achieve disinfection when used on luer connectors by integrating disinfectant or antimicrobial agent in the second cavity 40 of insert 30 or cavity 28 of the cap 10. The disinfectant or antimicrobial agent can be directly included in the cavity 28 or second cavity 40 of insert 30 or disinfectant or antimicrobial agent can be absorbed into sponges or foam material that fills the second cavity 40 of insert 30, specifically the absorbent reservoir material 50. Cap 10 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent reservoir material 50 and sealing foam 55 toward the top wall 25 of housing 20 upon connection to the female luer connector or the male luer connector allows the connector to contact the disinfectant or antimicrobial agent to disinfect the female luer connector or the male luer connector. Compression of the absorbent reservoir material 50 causes the antimicrobial or disinfectant to be excreted from the absorbent reservoir material 50, thereby disinfecting the female luer connector or the male luer connector.

In one or more exemplary implementation, in addition to the sealing foam 55, a peel seal 60 can be provided to seal the opening 27 prior to use of cap 10, for example, by attachment to a surface of a rim 29 of an open bottom 23 of housing 20.

Referring to FIG. 7, in one or more embodiments, the peelable seal 60 is disposed on the rim 29 of open bottom 23 of housing 20 to prevent the disinfectant or the antimicrobial agent from exiting the cavity 28. The peelable seal 60 further ensures sterility of the housing 20. With the absorbent reservoir material 50 properly inserted into the cavity 28 of the cap 10, the peelable seal 60 may be secured to the rim 29 of open bottom 23 of housing 20. The peelable seal 60 minimizes entry of potential particulate hazard and also provides a substantially impermeable enclosure for the cap 10. The peelable seal 60 provides a leak prevention and protection enclosure, protects the contents of absorbent reservoir material 50 contained within the cavity 28, and/or maintains a sealed, sterilized environment. The peelable seal 60 provides a sufficient seal at a range of temperatures, pressures, and humidity levels.

In one or more embodiments, the peelable seal 60 comprises an aluminum or multi-layer polymer film peel back top. In a specific embodiment, the peelable seal 60 is heat-sealed or induction sealed to the open end of the cap. In one or more embodiments, the peelable seal 60 comprises a moisture barrier. In one or more embodiments, the cap may be made of a high density polyethylene (HDPE) or polypropylene (PP) material. In one or more embodiments, the cap has an average wall thickness that separates the interior volume from the exterior surface in contact with the atmosphere of >0.03 inches. The combination of high barrier film, cap material and wall thickness is sufficient to prevent a significant amount of ethylene oxide (ETO) molecules to penetrate into the cap. This allows one or more embodiments of the sealed cap assembly to be sterilized with ethylene oxide, which is common with kit packs.

In an exemplary implementation of embodiments of the present disclosure, insert 30 may include two or more cantilevered prongs 37 having one or more gaps or cutouts 35. In an exemplary implementation, at least a portion of one or more of the two or more cantilevered prongs 37 of insert 30 may bend in order to allow better interference fit compliance with the fitting such as at least one of male connector or female connector.

In yet another exemplary implementation, insert 30 can extend essentially from top wall 25 of cavity 28 toward bottom of housing 20.

In still further exemplary implementation, insert 30 can extend essentially parallel to cylindrical sidewall 26 of housing 20.

In still yet further exemplary implementation, a profile of the inner thread 36 and/or the inner surface 31 can extend essentially parallel, or coincide with, a profile of the outer thread 38 and/or the outer surface 33, respectively.

Referring to FIGS. 1 through 8, according to exemplary embodiments of the disclosure, cap 10 can receive a tip or hub of a female needleless connector, for example after a peelable 60 sealing cavity 28 is removed or when the peelable seal 60 is pierced, within cavity 28 and secure, for example, threadedly, the tip of needleless connector 70 within inner portion 32 of cavity 28. One or more threads 36 can be sufficient to interlock with a hub or tip of needleless connector.

Referring further to FIGS. 1 through 8, according to exemplary embodiments of the disclosure, cap 10 can receive a tip or hub of an open lumen luer connector.

In an exemplary implementation of FIGS. 3 and 4, insert 30 is illustrated as comprising two prongs spaced by cutouts 35 and extending essentially from the closed end 39 of insert 30. However, also within the scope of the disclosure are caps comprising a unitary insert 30 without any cutouts 35, and caps having insert 30 comprising any number of identical and/or different (in any dimensional characteristics, such as length width, thickness, or shape) prongs, as long as insert 30 is configure to engage a female connector with respect to its inner surface, and engage a male connector with respect to its outer surface.

Referring to FIGS. 1 and 2, in one or more embodiments, the exterior surface of sidewall 26 comprises a plurality of grip members 90.

The cap 10 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 10 comprises a polypropylene or polyethylene material.

Figure 15:
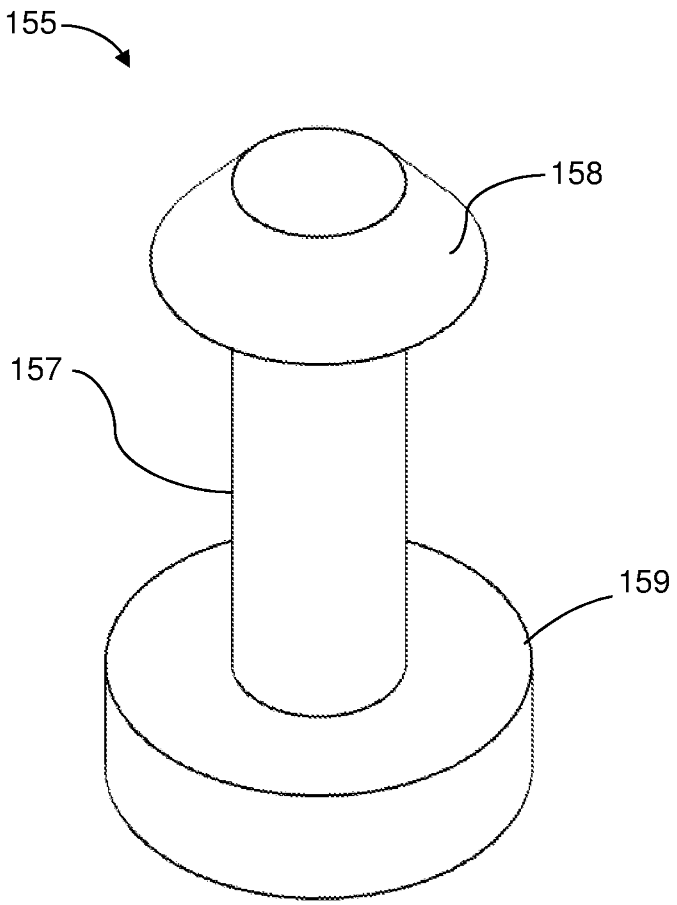
FIG. 15 illustrates a perspective top view of an exemplary piston-shaped sealing foam according to a second embodiment of the disclosure.
Figure 16:
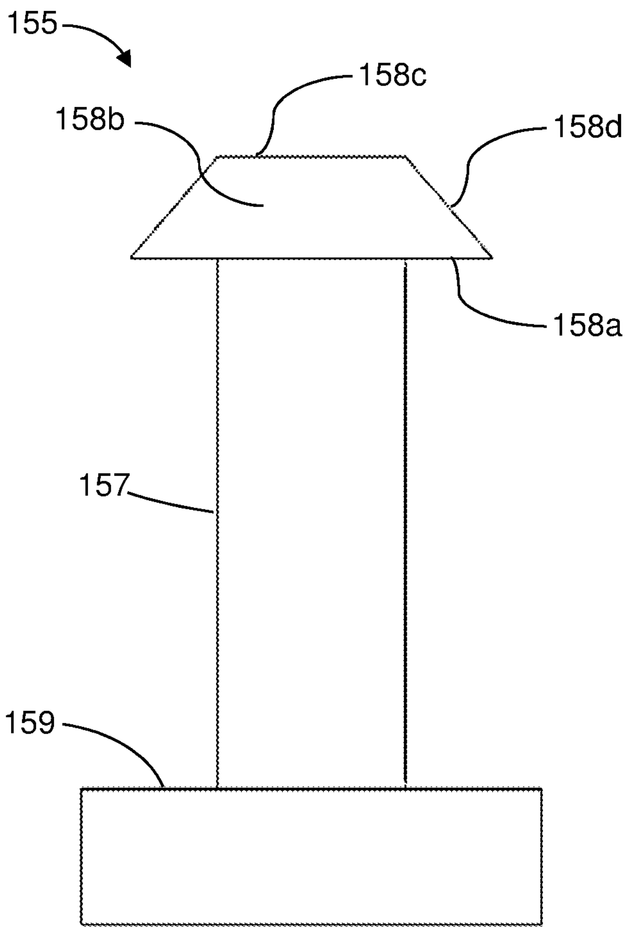
FIG. 16 illustrates a side view of an exemplary piston-shaped sealing foam according to a second embodiment of the disclosure.
Figure 17:
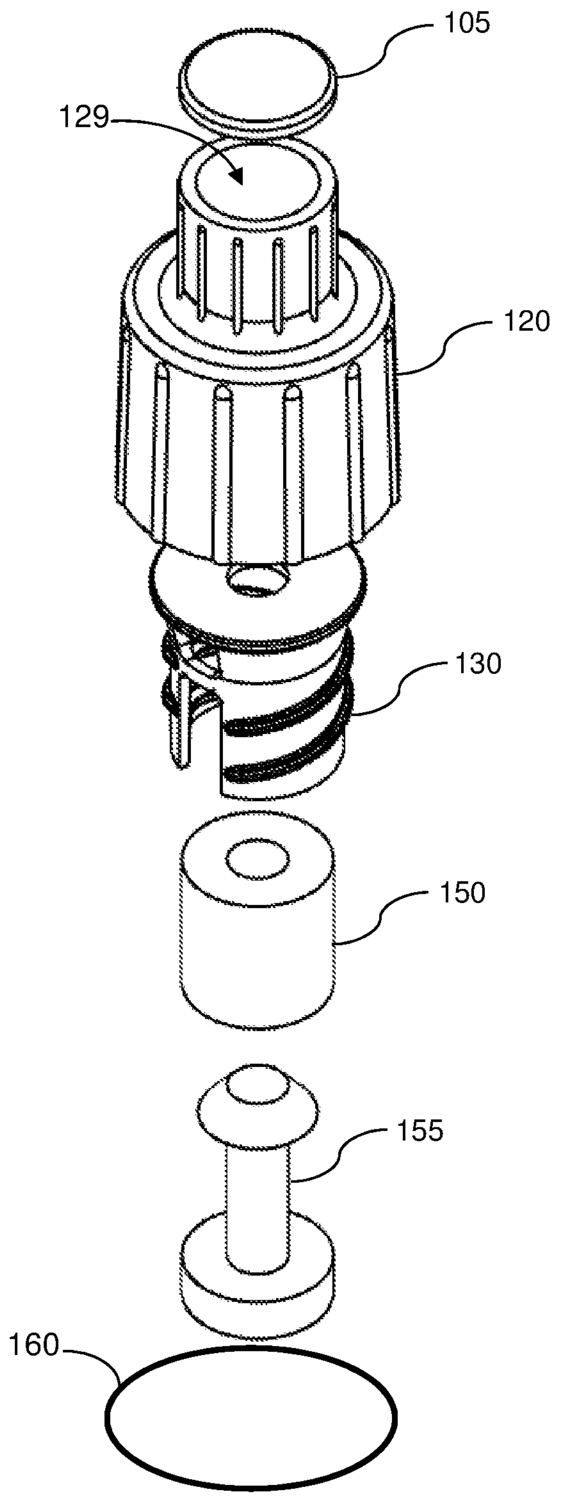
FIG. 17 illustrates an exploded view of an exemplary cap according to one or more embodiments of a second aspect of the disclosure.

A second aspect of the present disclosure, as shown in FIGS. 9 through 19, relates to a cap including a housing, an insert and absorbent material. An exploded view of a cap of the second aspect of the present disclosure, as shown in FIG. 17, relates to a cap 110 including a housing 120, an insert 130, an absorbent material 150, and piston-shaped sealing foam 155.

Figure 9:
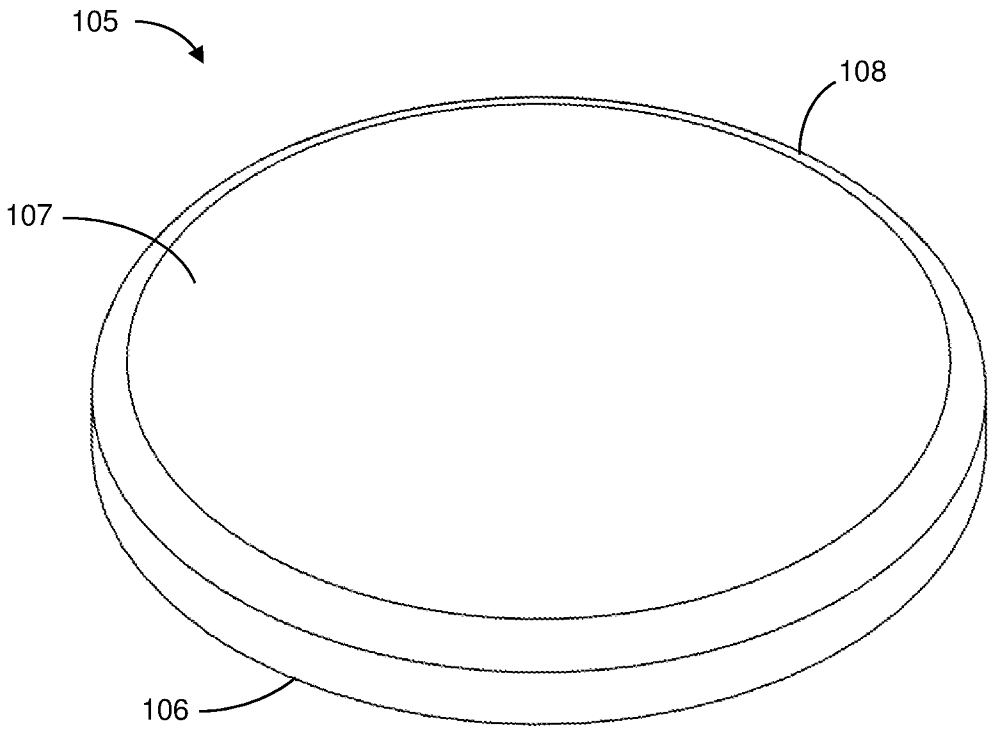
FIG. 9 illustrates a perspective top view of an exemplary cover according to a second exemplary embodiments of the disclosure.

Referring to FIG. 9, a cap 105 can include an annular body 108 with a covering surface 106 and a protective surface 107.

Figure 10:
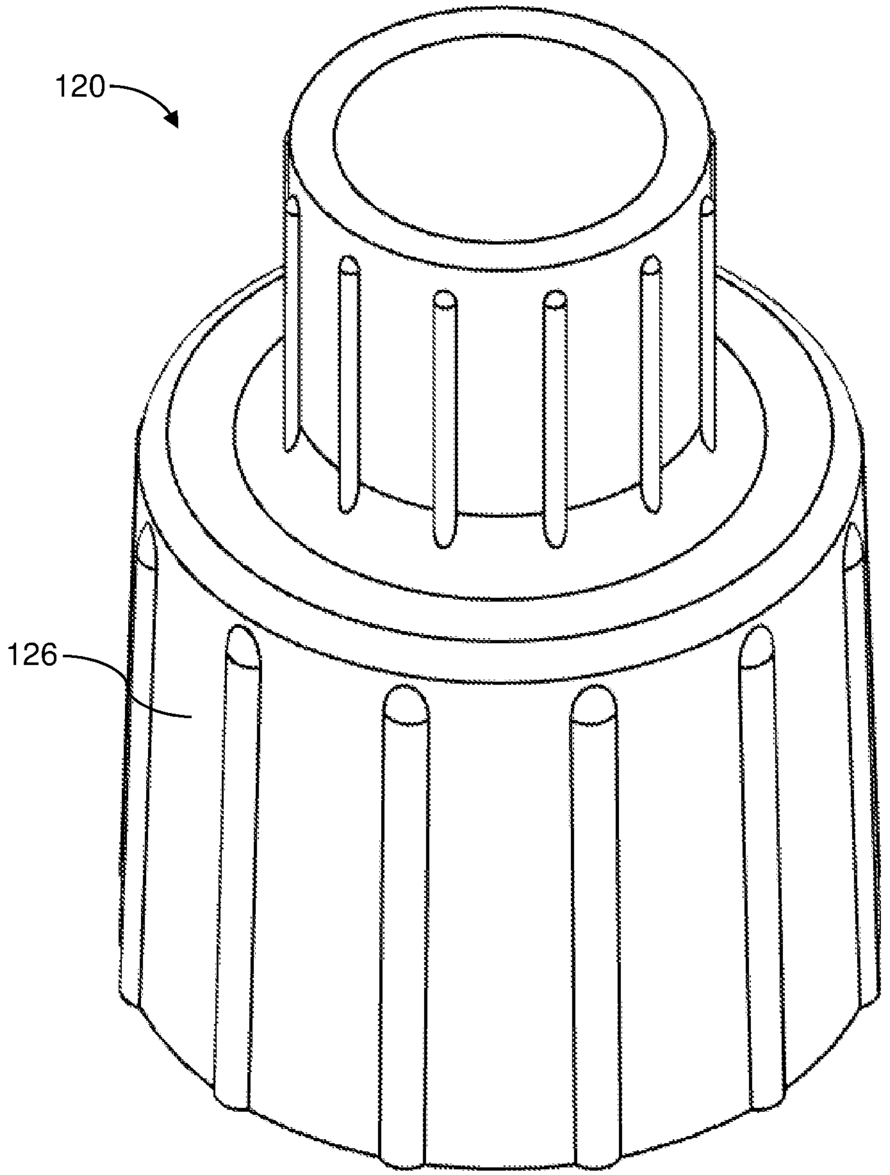
FIG. 10 illustrates a perspective top view of a housing according to a second exemplary embodiment of the disclosure.
Figure 11:
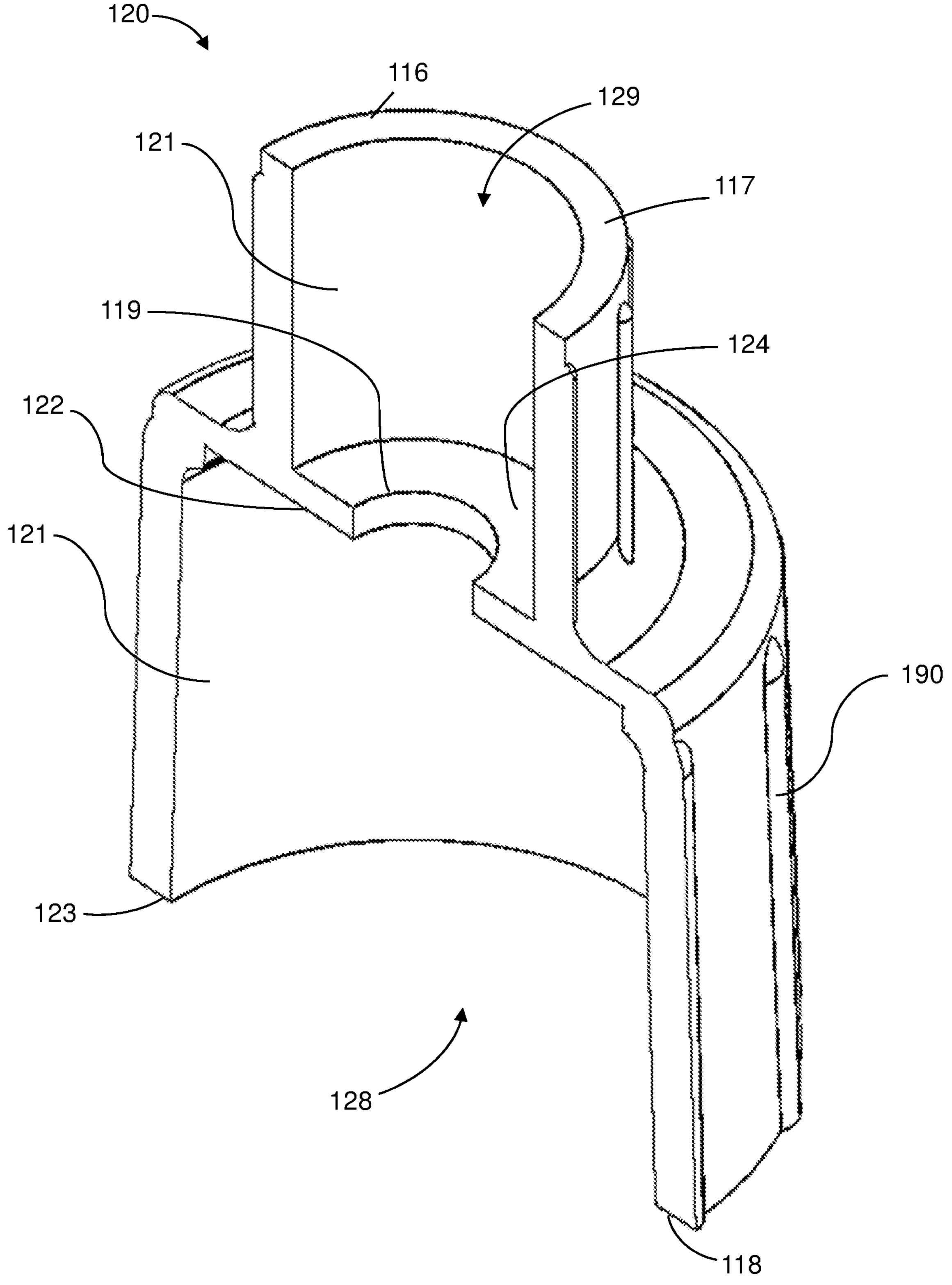
FIG. 11 illustrates a cross sectional view of the housing as shown in FIG. 10.

As shown in FIGS. 10 and 11, housing 120 comprises a proximal portion and a distal portion, the proximal portion includes an essentially frusto-conically shaped sidewall 126 with an inner surface 121 bounded by a rim 118 located at a distal end and an end face 117 located at a proximal end. Adjacent to the rim 118 is an open bottom 123. A first cavity 128 of the housing 120 is formed by the cylindrical sidewall 126 with an open bottom 123 forming a first cavity 128. The first cavity 128 within the housing 120 is configured for receiving a hub of a female needleless connector or a male needleless connector. Opposite to the open bottom 123 of the first cavity 128 is a top wall 122, the top wall being positioned between the proximal portion and distal portion. Adjacent to the end face 117 is an open top 116, defining a tertiary cavity 129 that is formed by the cylindrical sidewall 126 of the housing 120. Opposite to the open top 166 of the tertiary cavity 129 is a bottom wall 124. An aperture 119 exists between the bottom wall 124 and the top wall 122 of the housing 120, creating a fluid path between the first cavity 128 and the tertiary cavity 129. Referring to FIGS. 10-11 the first cavity 128 of housing 120 is in fluid communication with a tertiary cavity 129 of housing 120 via the aperture 119. The exterior surface of sidewall 126 comprises a plurality of grip members 190.

As shown in FIG. 17, the cap 105 is configured to cover the tertiary cavity 129 of the housing 120. In one or more embodiments, the covering surface 106 of the cap 105 is bonded to the end face 117 of the housing 120.

Figure 12:
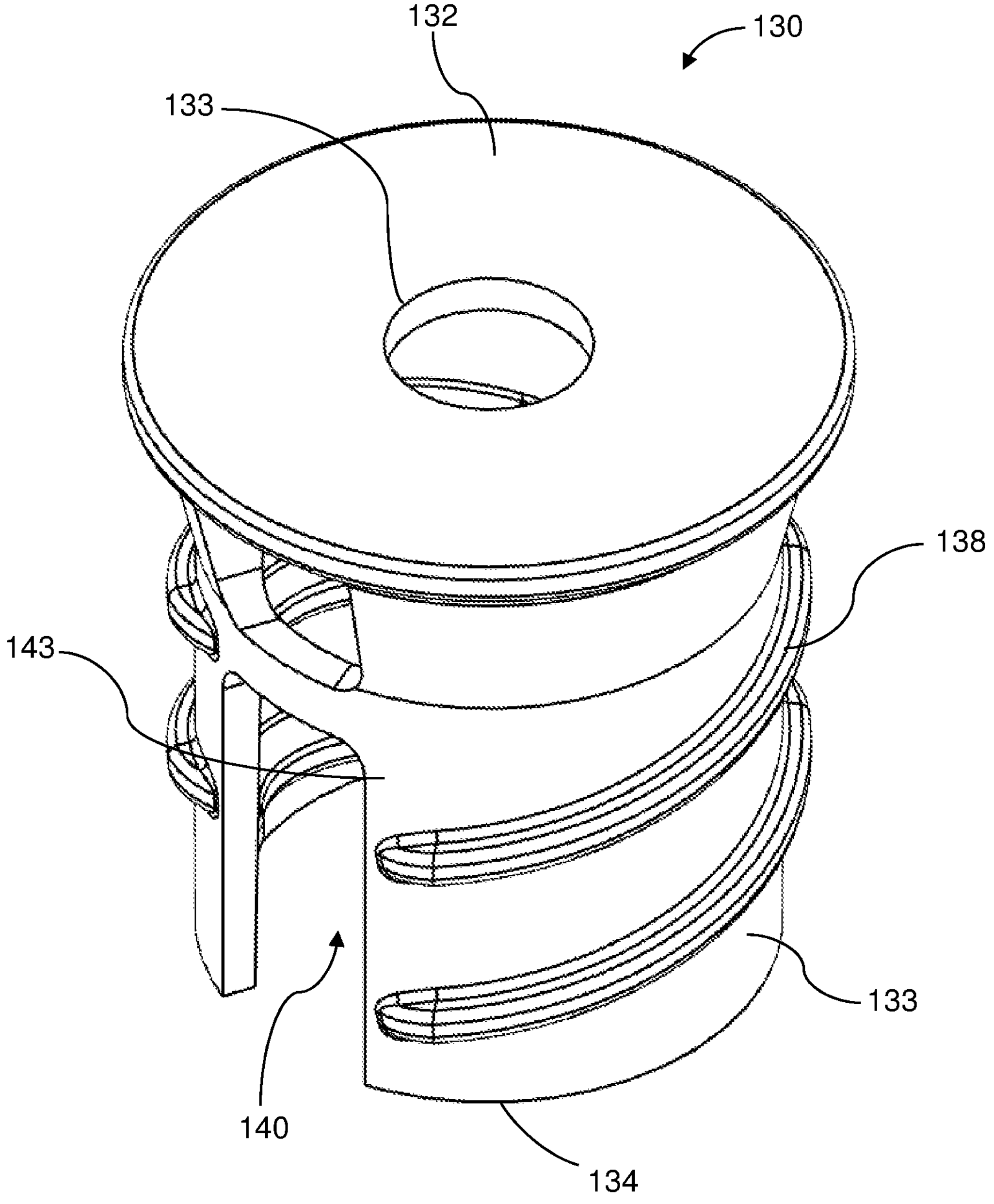
FIG. 12 illustrates a perspective top view of an exemplary insert according to a second embodiment of the disclosure.
Figure 13:
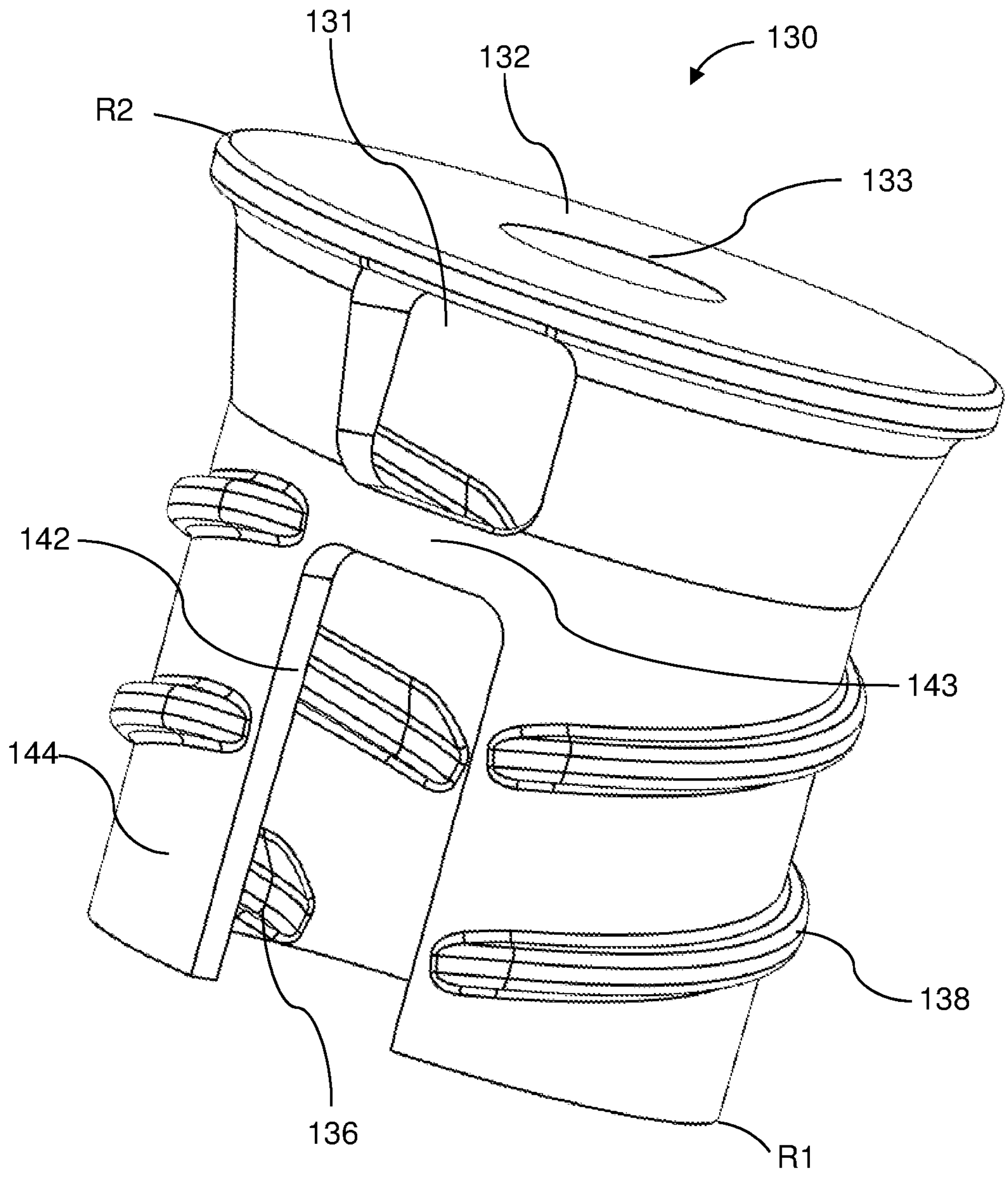
FIG. 13 illustrates a perspective side view of the insert as shown in FIG. 12.

As shown in FIGS. 12 and 13, insert 130 can include a distal wall 132 having a centrally disposed opening 133, an open proximal end 139, a sidewall extending proximally from the distal wall 132 toward the open proximal end 139. In one or more embodiments, the insert 130 is the form of a split-thread prong, the split-thread insert having an inner surface 131 and an outer surface 137. The inner surface 131 of the split-thread insert 130 defines a second cavity 140.

In one or more embodiments, an outer thread 138 can be included on the outer surface 138 of the split-thread insert 130, the outer thread 138 being sufficient to interlock with a mating feature of the female needleless connector.

In one or more embodiments, as shown in FIGS. 12 and 13, the split-thread insert 130 can include one or more cantilevered prongs separated by one or more respective gaps 142, in which at least one of the prongs configure to bend to facilitate interference fit between the insert 130 and the mating feature of the male needleless connector or female needleless connector. In one or more embodiments, the insert 130 further includes one or more bridge sections 143 arranged to span between the one or more gaps 142 of the one or more cantilevered prongs of the split-thread insert 130.

The sidewall of the insert 130 comprises an upper portion and a lower portion. In one or more embodiments, as shown in FIGS. 12-13, the lower portion of the sidewall tapers outward toward the distal wall 132 and the lower portion of the sidewall can be cylindrical.

As shown in FIG. 12-13, to provide a better rigidity, in an embodiment according to the present disclosure, bridge sections 143 can be arranged between at least parts of the prongs 144 or optionally between all of the prongs 144. The bridge section 143 is generally formed from the same material as the prongs 144 and housing 120. In one or more embodiments, prongs 144 and bridge sections 143 are molded as a whole piece. The bridge sections 143 are configured to provide for improved rigidity, giving structural integrity to prongs 144 and permit less material to be used during the manufacturing step of the cap. A good rigidity is achieved when the bridge sections are arranged substantially between the distal ends of the prongs 144. In one or more embodiments; the bridge sections 143 are configured to limit defection of the prongs 144.

As shown in FIG. 13, the sidewall of split-thread insert 130 has a radius R1, which substantially corresponds to a radius of the neck element of a male or female connector. The sidewall of the split-thread insert 130 tapers outwardly and extends to a radius R2 which is larger than the radius R1 of the split-thread insert 130. The radius R2 corresponds substantially to the largest radius of the split-thread insert 130.

In an exemplary implementation of embodiments of the present disclosure, insert 130 can be cantilevered, for example by having one or more gaps or cutouts 135. In an exemplary implementation, at least a portion of the a cantilevered insert 130 may bend or deflect in order to allow better interference fit compliance with the fitting such as at least one of male connector or female connector.

Figure 18:
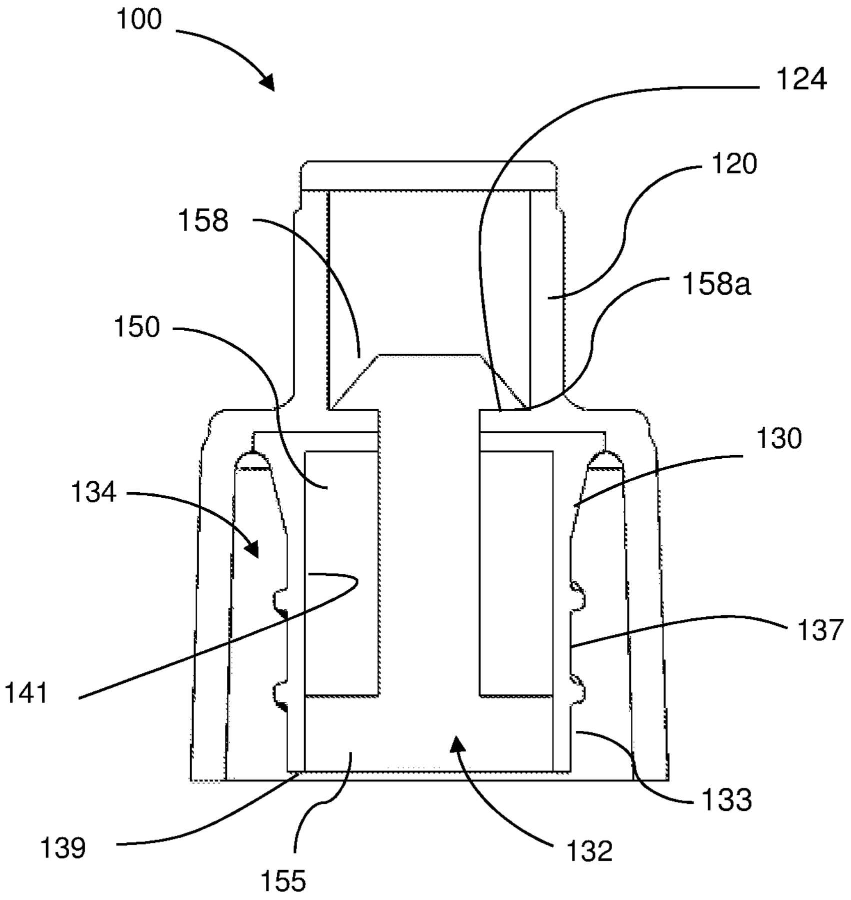
FIG. 18 illustrates a cross-sectional view of an exemplary assembled cap as shown in FIG. 17 having the piston-shaped sealing foam in an initial state.
Figure 19:
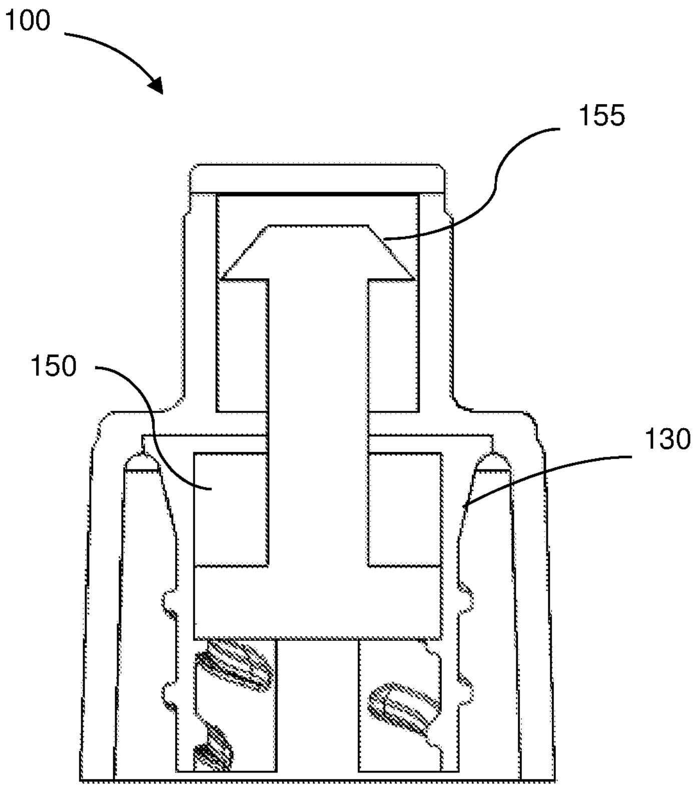
FIG. 19 illustrates a cross-sectional view of an exemplary assembled cap as shown in FIG. 18 showing the position of the piston-shaped sealing foam after an open lumen connector has been attached.

In yet further exemplary implementation, inner portion 141 of cavity 128 can extend further into the cap toward inner surface 125 of top wall 122 than the outer portion 134, for example as illustrated in the cross section views of FIGS. 18 and 19.

In an exemplary implementation of FIGS. 12 and 13, insert 130 is illustrated as comprising two prongs spaced by gaps 142 and extending essentially from distal wall 132. However, also within the scope of the disclosure are caps comprising a unitary insert 130 without any gaps 142, and caps 105 having insert 130 comprising any number of identical and/or different (in any dimensional characteristics, such as length width, thickness, or shape) prongs, as long as insert 130 is configure to engage a female connector with respect to its inner surface, and engage a male connector with respect to its outer surface.

FIGS. 12 and 13 show the split-thread insert 130 showing the thread pattern of internal thread 136 and outer thread 138.

As shown in FIGS. 12 and 13, outer threads 138 on the outer sidewall of the split-thread insert 130 extend in a helical pattern.

As shown in FIGS. 12 and 13, inner threads 136 on the inner sidewall of the split-thread insert 130 extend in a helical pattern.

As shown in FIGS. 17 through 19, in some embodiments, the insert 130 can be positioned within the first cavity 128. As shown in FIGS. 12 through 13, in some embodiments, the split thread insert 130 is disposed within cavity 128 having an inner surface 131 defining an inner portion 141 of cavity 128, and an outer surface 137 defining and outer portion 134 of cavity 128. In some embodiments, split-thread insert 130 comprises an inner thread 136 on its inner surface 131 for engaging a female connector and an outer thread 138 on its outer surface 137 for engaging a male connector.

In one or more embodiments, the split-thread insert 130 and the housing 120 can be bonded together through ultrasonic welding or solvent resistant biocompatible adhesive. In one or more embodiments, split-thread insert 130 and the housing 120 can also be interlocked through interference fit or snap fit. A ledge/wedge portion can be arranged at the distal ends of the split-thread insert 130 to provide for a snap on connection to the cap housing. In one or more embodiments, the inner surface 125 of the top wall 122 of housing 120 may have a recess into which the ledge/wedge of the insert may be inserted. In one or more embodiments, the centrally disposed opening 133 of the insert 130 is be coincident and concentric with the aperture 119 of the housing 120 upon being interlocked with one of the bonding method previously described.

As shown in FIG. 13, bridges 143 connecting the gaps 142 between the prongs 144 restrict the angle of the deflection of the prongs 144, increasing the security of engagement when the disinfecting cap is connected to male or female connectors.

In one or more embodiments, full length or partial length of the prongs 144 may be threaded to control how deep the connectors can be threaded into the cavity. This may also facilitate the volume of compression on IPA impregnated sponges to control the IPA volume that's dispensed upon engagement to connectors.

In one or more embodiments, as shown in FIGS. 15 and 16, sealing foam 155 comprises an integral body formed by a sealing bottom 159, a head 158, and an elongate shaft 157. The sealing bottom 159 comprises of an integral body, an annular wall, a bonded surface and a sealing surface. The head 158 comprises of anti-removal surface 158*a*. The head is shaped like a tapered cylinder. The pressure surface 158*b* of the head 158 comprises of a top surface 158*c* and a tapered surface 158*d*. The head 158 and the sealing bottom 159 are integrally connected by an elongate shaft 157. The elongate shaft comprises two ends; whereby one end of the elongate shaft is concentrically connected to the anti-removal surface 158*a* of the head 158 and the opposite end is secured to the center of the sealing bottom 159. The sealing foam is in the shape of a plunger/piston.

In a specific embodiment, the sealing foam is closed cell foam. In one or more embodiment the sealing foam may comprise of closed cell foams such as PE foams or TPE foams. The sealing foam may also comprise of rubber or rubber like foams including: EPDM sponges, EVA, Buna-N, polyethylene sponges, silicone, vinyl, neoprene, fluoroelastomers, gum rubber, or TPE materials. In one or more embodiments, the sealing foam is molded or extruded or die cut from sheeting to form a cylindrical block shape.

Figure 14:
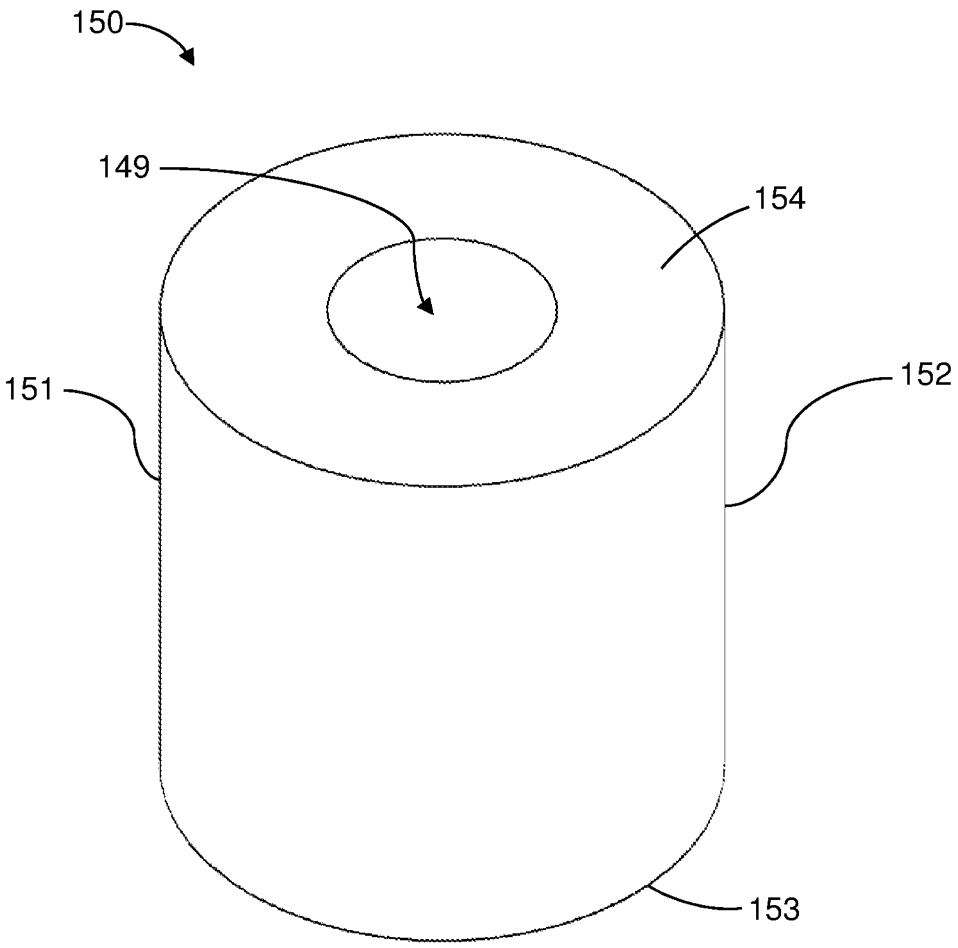
FIG. 14 illustrates a perspective top view of an exemplary absorbent reservoir material according to a second embodiment of the disclosure

As shown in FIG. 14, surrounding the elongate shaft 157 of the sealing foam 155 is the absorbent reservoir material 150. The absorbent reservoir material 150 comprises an integral body 151, an annular wall 152, a bottom surface 153, and a distal face 154. The absorbent reservoir material 150 also comprises of a centrally disposed opening 149 that is positioned concentrically relative to the annular wall 152 and completely extends from the bottom surface 153 to the distal face 154 of the absorbent reservoir material 150. The elongate shaft 157 of the sealing foam 155 is disposed into the opening 149 of the absorbent reservoir material 150.

The absorbent reservoir material 150 may be soaked with a disinfectant or an antimicrobial agent. In one or more embodiments the absorbent reservoir material 150 is a nonwoven material, foam, or a sponge. In a specific embodiment, the absorbent reservoir material 150 is polyethylene foam. The foam may be open celled, semi-opened or closed celled and may be molded or extruded or die cut from sheeting. In one or more embodiments, the absorbent reservoir material 150 is molded or extruded or die cut from sheeting to form a cylindrical block shape.

The absorbent reservoir material 150 surrounds the elongate shaft 157 of the sealing foam 155. The sealing foam 155 and the absorbent reservoir material 150 are positioned within the inner surface 131 of insert 130 defining a second cavity 140 where the sealing surface 159 will be in contact with the lumen of open luer connectors.

As shown in FIG. 18, the elongate shaft 157 of the sealing foam 155 is positioned in the centrally disposed opening 133 of the distal wall 132 of the insert 130. The head 158 of the sealing foam 155 points towards the cap 105 and the sealing bottom 159 of the sealing foam 155 points towards the open bottom 123 of the housing 120. As shown in FIG. 18, when there is no connector secured to the cap, the anti-removal surface 158*a* of the sealing foam 155 is abutted to the bottom wall 124 of the housing 120. This prevents the sealing foam 155 to be removed from the cavity 128 of the housing 120.

The head 158 positioned at the distal end of the elongate shaft 175 is in the form of a tapered cylinder, the tapered cylinder tapering from a proximal base to a distal end of the tapered cylinder, wherein the narrow side points on the proximal base abut the closed end of the cap. However, the head 158 can be in the shape of a tetrahedron, sphere, hemisphere, or any other shape that can prevent the head 158 to be removed from the tertiary cavity 129 of the housing 120.

FIG. 19 illustrates a cross-sectional view of an exemplary assembled cap shown in FIG. 18 showing the position of the piston-shaped sealing foam after an open lumen connector has been attached and pressure is applied to the sealing foam 155 and absorbent reservoir material 150. Advancement of the head 158 causes fluid flow between the tertiary cavity 129 of the housing 120 and the cavity 128 of the housing 120.

The absorbent reservoir material 150 serves as a disinfecting member, such as an IPA soaked sponge and/or sponge. In one or more embodiments, absorbent material 150 may be in the form of one or more sponge(s) formed together as a single cleaning member or formed separate as multiple cleaning members, can be provided within cavity 128, for example in the proximity of the top wall 122 of inner portion 141 and/or towards top of outer portion 134 of cavity 128.

The cap 110 can achieve disinfection when used on luer connectors by integrating disinfectant or antimicrobial agent in the cavity 128 of the cap 110. The disinfectant or antimicrobial agent can be directly included in the absorbent reservoir material 150 or disinfectant or antimicrobial agent can be absorbed into sponges or foam material that fills the cap 110. Cap 110 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 150 toward the top wall 122 of housing 120 upon connection to the female luer connector or the male luer connector allows the connector to contact the disinfectant or antimicrobial agent to disinfect the female luer connector or the male luer connector. Compression of the absorbent material 150 causes secretion of disinfectant or antimicrobial agent from the absorbent material 150.

Referring to back to FIG. 11, rim 118 of an open bottom 123 of housing 120 defines an engagement surface where a peelable seal 160 may be secured.

Referring to FIG. 17, in one or more embodiments, the peelable seal 160 is disposed on the engagement surface of open bottom 123 of housing 120 to prevent the disinfectant or the antimicrobial agent from exiting the cavity 128 or second cavity 140 of insert 130. With the absorbent material 150 properly inserted into the second cavity 140 of insert 130, the peelable seal 160 may be secured to the engagement surface of open bottom 123 of housing 120. The peelable seal 160 minimizes entry of potential particulate hazard and also provides a substantially impermeable enclosure for the cap 110, provides a leak prevention and protection enclosure, protects the contents of absorbent material contained within the cavity 128, and/or maintains a sealed, sterilized environment. The peelable seal 160 provides a sufficient seal at a range of temperatures, pressures, and humidity levels.

In one or more embodiments, the peelable seal 160 comprises an aluminum or multi-layer polymer film peel back top. In a specific embodiment, the peelable seal 160 is heat-sealed or induction sealed to the end face of the locking lid or to the cap open end. In one or more embodiments, the peelable seal 160 comprises a moisture barrier.

In an exemplary implementation, a peelable sealing film 160 can be provided to seal the opening 127 prior to use of cap 110, for example, by attachment to a surface of a rim 118 of an open bottom 123 of housing 120, as described for example in the above-referenced prior applications.

The cap 110 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 110 comprises a polypropylene or polyethylene material.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

Figure 20:
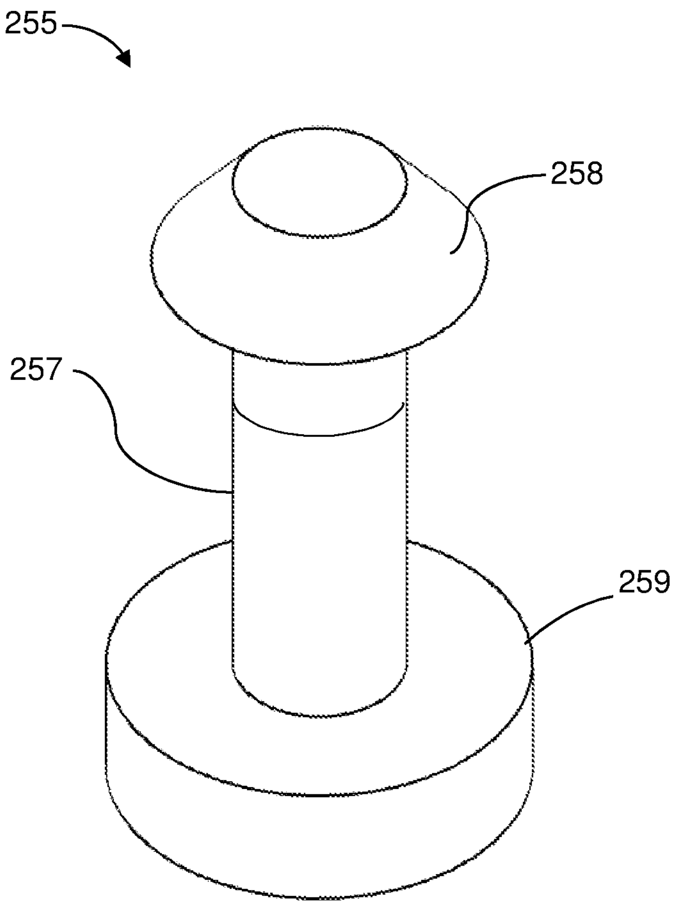
FIG. 20 illustrates a side view of an exemplary piston-shaped sealing foam according to a third embodiment of the disclosure.
Figure 21:
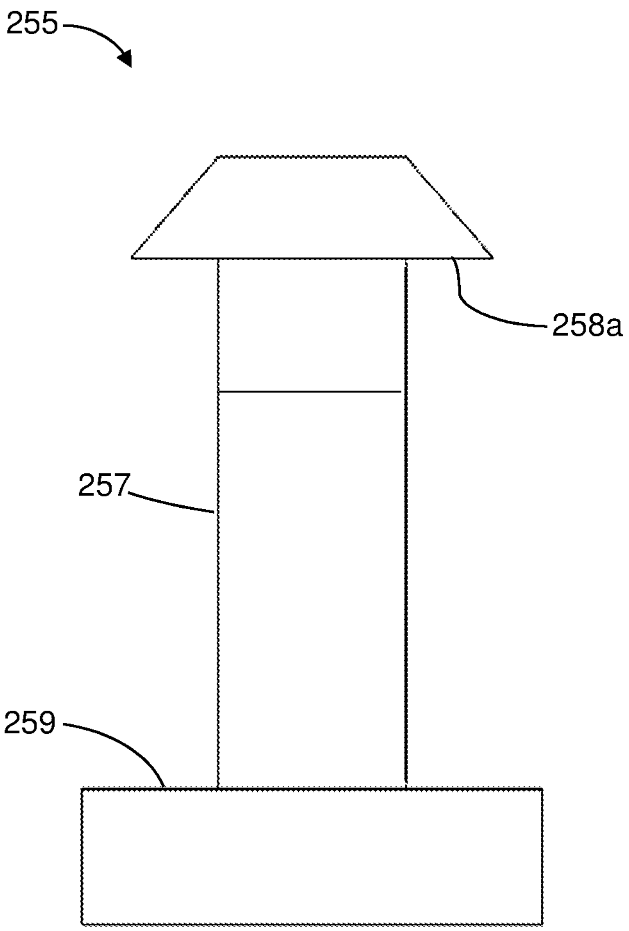
FIG. 21 illustrates a perspective top view of an exemplary piston-shaped sealing foam according to a third embodiment of the disclosure.

A third aspect of the present disclosure pertains to an alternate embodiment of the sealing foam. As shown in FIGS. 20 and 21, in one or more embodiments, sealing foam 255 may be composed of segments made of different materials. For example, a portion or the entire elongate shaft may be a nonwoven material, foam, or a sponge. In a specific embodiment, the elongate shaft 257 is polyethylene foam. The foam may be open celled, semi-opened or closed celled. While the head 258 and the bottom seal 259 of the sealing foam may comprise of closed cell foams such as PE foams or TPE foams. The head 258 and the bottom seal 259 of the sealing foam 255 may also comprise of rubber or rubber like foams including: EPDM sponges, EVA, Buna-N, polyethylene sponges, silicone, vinyl, neoprene, fluoroelastomers, gum rubber, or TPE materials.

In an alternate embodiment, the anti-removal surface **258*a* of the head 258 of the sealing foam 255** can be affixed to the cap body—preventing the bottom seal of the sealing foam from getting stuck in open lumens of access ports, e.g., intravenous male connectors and stopcocks.

Figure 22:
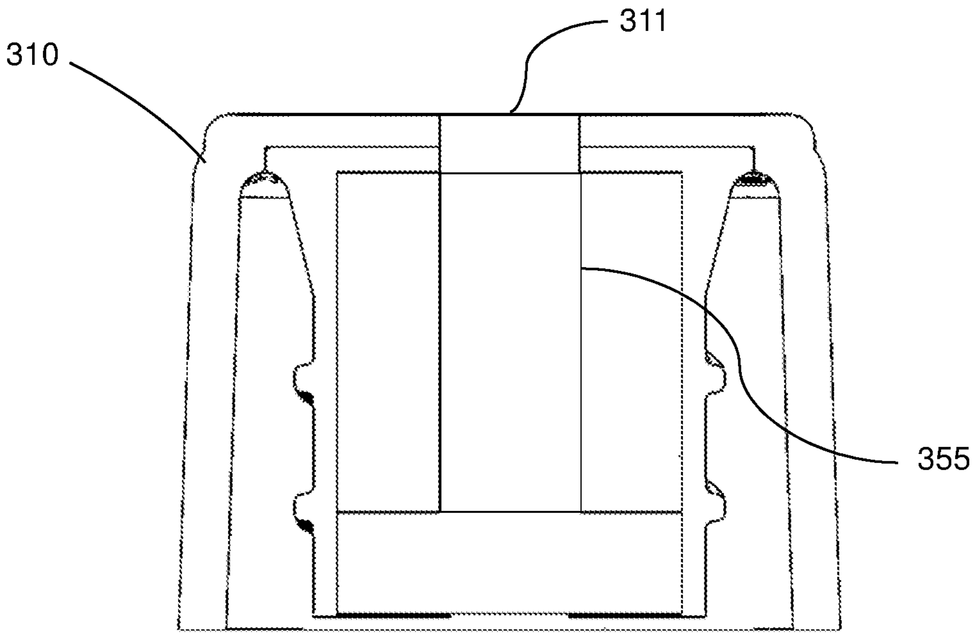
FIG. 22 illustrates a cross-sectional view of an exemplary cap according to one or more embodiments of a fourth aspect of the disclosure.

A fourth aspect of the present disclosure pertains to yet another alternate embodiment of the sealing foam 355. As shown in FIG. 22, the distal end of the elongate shaft of the sealing foam can be affixed to the closed end 311 of the cap 310.

A fifth aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the insert of the present disclosure upon insertion of the medical connector into the cap such that the medical connector contacts the absorbent material and the disinfectant or antimicrobial agent.

The exemplary caps of the present disclosure are capable of capable of blocking the lumens of open luers to minimize ingress of disinfectant and microbial agents into connectors, thereby reducing risk of the disinfectant and microbial agents entering the blood stream of a patient.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cap comprising:

a housing comprising
  a top wall,
  a cylindrical sidewall forming a first cavity, and
  an open bottom formed by the cylindrical sidewall with an opening to the first cavity within the housing for receiving a needleless connector having an open lumen;

an insert disposed in the housing and positioned within the first cavity, the insert having an inner surface and an outer surface, the inner surface of the insert defining a second cavity,
  an inner thread on the inner surface of the insert and an outer thread on the outer surface of the insert;

an absorbent reservoir material disposed under radial compression by the inner thread on the inner surface of the insert, the absorbent reservoir material having an integral body, an annular wall, a bottom surface, and a distal face; and a sealing foam is disposed onto absorbent reservoir material, the sealing foam having an integral body, an annular wall, a bonded surface and a sealing surface, the bonded surface of the sealing foam is secured to the bottom surface of the absorbent reservoir material such that the annular walls of both the sealing foam and the absorbent reservoir material are concentric and coincident, wherein the bonded surface of the sealing foam is secured to the bottom surface of the absorbent reservoir material using adhesives, heat welding, or ultrasonic welding, and wherein the sealing foam sustains a fluid pressure of the open lumen of the needleless connector to prevent fluid leakage.

2. The cap of claim 1, wherein the absorbent reservoir material is a nonwoven material, foam, or a sponge.

3. The cap of claim 1, wherein the absorbent reservoir material is soaked with a disinfectant or an antimicrobial agent.

4. The cap of claim 1, wherein the sealing foam is made of a closed cell foam.

5. The cap of claim 4, wherein the sealing foam is made of a polyethylene foam.

6. The cap of claim 4, wherein the sealing foam is made of a thermoplastic elastomer.

7. The cap of claim 4, wherein the sealing foam is made of a rubber or rubber like foams.

8. The cap of claim 7, wherein the sealing foam is an EPDM sponges, EVA, Buna-N, silicone, vinyl, neoprene, fluoroelastomers, gum rubber.

9. The cap of claim 1, wherein the insert extends essentially from an inner surface of the top wall toward the open bottom of the housing.

10. The cap of claim 1, wherein the insert extends essentially parallel to the sidewall of the housing.

11. The cap of claim 1, wherein the inner thread and the outer thread have an inclined thread pattern.

12. The cap of claim 1, wherein the inner thread and outer thread have a helical-shaped thread pattern.

13. The cap of claim 1, wherein an exterior wall surface of the sidewall of the housing includes a plurality of grip members.

14. The cap of claim 1, further comprising a disinfectant or an antimicrobial agent.

15. The cap of claim 14, wherein the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

16. The cap of claim 1, wherein the housing is made of a high density polyethylene or polypropylene material.

17. The cap of claim 1, wherein the housing has an average wall thickness of >0.03 inches.

18. The cap of claim 1, further comprising a peelable seal.

19. The cap of claim 18, wherein the peelable seal comprises an aluminum or multi-layer polymer film.

20. The cap of claim 18, wherein the peelable seal further comprises a moisture barrier.

* * * * *